US012784876B2

(12) United States Patent
Krmc et al.

(10) Patent No.: US 12,784,876 B2
(45) Date of Patent: Nov. 3, 2026

(54) SYSTEMS AND METHODS FOR PLANT PROCESS OPTIMIZATION

(71) Applicant: JEMS, ENERGETSKA DRUZBA, D.O.O., Ljubljana (SI)

(72) Inventors: Johannes J. Krmc, Škocjan (SI); Mitja Jermol, Ljubljana (SI); Ervin Pfeifer, Škofljica (SI); Suzana Leben, Škofja Loka (SI)

(73) Assignee: JEMS, ENERGETSKA DRUZBA, D.O.O., Ljubljana (SI)

(*) Notice: Subject to any disclaimer, the term of this patent is extended or adjusted under 35 U.S.C. 154(b) by 629 days.

(21) Appl. No.: 18/273,371

(22) PCT Filed: Jan. 20, 2022

(86) PCT No.: PCT/EP2022/051263

§ 371 (c)(1),
(2) Date: Jul. 20, 2023

(87) PCT Pub. No.: WO2022/157257

PCT Pub. Date: Jul. 28, 2022

(65) Prior Publication Data

US 2024/0047015 A1 Feb. 8, 2024
US 2025/0232843 A2 Jul. 17, 2025

(30) Foreign Application Priority Data

Jan. 20, 2021 (GB) ..................................... 2100758

(51) Int. Cl.
*G16C 20/10* (2019.01)

(52) U.S. Cl.
CPC .................................... *G16C 20/10* (2019.02)

(58) Field of Classification Search
CPC .. G16C 20/10; G05B 13/048; G05B 13/0265; G05B 13/04; G05B 19/41885
See application file for complete search history.

(56) References Cited

U.S. PATENT DOCUMENTS 10,877,470 B2 12/2020 Burd et al.
11,454,947 B2 * 9/2022 Pirker .................. G05B 19/406
(Continued)

FOREIGN PATENT DOCUMENTS

CA 2474523 6/2005
DE 10049377 4/2002
(Continued)

OTHER PUBLICATIONS

International Search Report, dated May 19, 2022, from corresponding International Application No. PCT/EP2022/051263.
(Continued)

*Primary Examiner* — Brian J. Sines
(74) *Attorney, Agent, or Firm* — Thomas | Horstemeyer, LLP

(57) ABSTRACT

A control system for optimising a fuel generation process performed by a synthetic fuel generation plant. The system comprises an interface unit configured to be communicably coupled to the synthetic fuel generation plant; a digital twin representative of the synthetic fuel generation plant; and an optimisation unit in communication with the interface unit and the digital twin. The optimisation unit is configured to perform an optimisation process to determine, from an initial state of the synthetic fuel generation plant, an updated state of the fuel generation plant using the digital twin.

20 Claims, 10 Drawing Sheets

(56) References Cited

U.S. PATENT DOCUMENTS

| | | | | |
|---|---|---|---|---|
| 2011/0020183 | A1 | 1/2011 | Storchi et al. | |
| 2014/0310228 | A1* | 10/2014 | Nakabayashi | G06N 7/01 706/52 |
| 2018/0210436 | A1* | 7/2018 | Burd | G05B 19/41885 |
| 2022/0057786 | A1* | 2/2022 | Phan | G06N 3/08 |

FOREIGN PATENT DOCUMENTS

| | | |
|---|---|---|
| DE | 10356245 | 7/2005 |
| DE | 102005056735 | 8/2006 |
| DE | 102012022710 | 5/2014 |
| EP | 1798274 | 6/2007 |
| EP | 3065008 | 9/2016 |
| KR | 101853480 | 4/2018 |
| WO | 2010/063248 | 6/2010 |
| WO | 2018/228619 | 12/2018 |
| WO | 2020/020481 | 1/2020 |

OTHER PUBLICATIONS

Written Opinion of the International Searching Authority, dated May 19, 2022, from corresponding International Application No. PCT/EP2022/051263.

* cited by examiner

SYSTEMS AND METHODS FOR PLANT PROCESS OPTIMIZATION

CROSS-REFERENCE TO RELATED APPLICATIONS

This application is a national phase entry of International Patent Application No. PCT/EP2022/051263, filed Jan. 20, 2022, which claims the benefit of United Kingdom Patent Application No. GB2100758.8, filed Jan. 20, 2021, the entire disclosures of which are incorporated herein by reference in their entirety.

FIELD OF INVENTION

Aspects of the present disclosure relate to optimisation of fuel generation plants. Specifically, but not exclusively, aspects of the present disclosure relate to the use of an optimisation process to provide improved control procedures to a synthetic fuel generation plant. Specifically, but not exclusively, the optimisation process utilises a digital twin of the synthetic fuel generation plant to predict the future state of the synthetic fuel generation plant.

BACKGROUND

Industrial growth is known to accelerate the production of waste and greenhouse gases, which are proven causes of climate change. Examples of waste include biomass, plastics, solid recovered fuel, used oil, sugar bagasse, rice husks, and the like. Current methods of handling such waste are becoming both increasingly complex and costly. These methods are not suitable or sustainable solutions for the projected increase in waste production over the coming years.

Many existing waste handling technologies are expensive, produce harmful gases, or are not yet industrially viable. In contrast, synthetic fuel generation plants transform any waste hydrocarbon material into a high quality synthetic fuel through a low temperature and low pressure chemical process. As such, synthetic fuel generation plants are able to transform waste materials in the form of solid and/or liquid hydrocarbons into fuel through an environmentally sustainable process.

One example chemical process used by synthetic fuel generation plants is the Catalytic Depolymerisation Process (CDP). A CDP process can convert organic matter such as wood, coal, crude oil, waste fuel, SRF, waste oil, plastics, paper, rubber, textile, yard trimmings, cultivated plants, agricultural residues and weed (e.g., *Arundo donax, calliandra*, empty fruit bunches, giant king grass, miscanthus, napier grass, olive cake, palm kernel, palm oil residues, rice husk, straw, sugar bagasse, and water hyacinth) into high-quality synthetic diesel, i.e., synthetic fuel.

Synthetic fuel generation plants are able to transform one ton of waste into 250 to 750 litres of fuel depending on type of the feedstock, with a speed of up to 1000 litres per hour or more depending on the size of the plant. Furthermore, synthetic fuel generation plants are environmentally friendly and do not produce harmful gasses like dioxins or furans. Moreover, synthetic fuel generation plants are $CO_2$ neutral-to-negative, producing synthetic fuel, no other gases than $CO_2$, sludge and distilled water. A synthetic fuel generation plant employing a catalytic depolymerisation process could decrease $CO_2$ emissions by up to 30%.

However, existing synthetic fuel generation plants require a high-degree of human input to maintain operation and ensure that the fuel generation process is operating efficiently. Furthermore, existing synthetic fuel generation plants require continuous adjustment in order to provide the above benefits whilst ensuring that a high quality and/or quantity of fuel is produced.

Plants employing a catalytic polymerisation process are known—e.g., as disclosed in DE10049377, DE102005056735, EP1798274A1, CA2474523A1, DE102012022710B4, DE10356245B4, WO2010/063248A2, WO2018/228619A1, and WO2020/020481A1—and these require extensive human input to run efficiently.

Accordingly, there is a need for systems to automate the control of synthetic fuel generation plants in order to maintain a high quality and/or quantity of fuel production.

Therefore, the present disclosure is directed to systems and methods for the control of synthetic fuel generation plants which aim to address some of the above identified problems.

SUMMARY OF INVENTION

According to an aspect of the present disclosure there is provided a control system for optimising a fuel generation process performed by a synthetic fuel generation plant. The system comprises an interface unit configured to be communicably coupled to the synthetic fuel generation plant. The interface unit is operable to obtain an initial state associated with the synthetic fuel generation plant, the initial state comprising state information indicative of a state of one or more processes of the synthetic fuel generation plant at an initial time point. The system further comprises a digital twin representative of the synthetic fuel generation plant. The digital twin comprising a trained machine learning model configured to receive a first state associated with the synthetic fuel generation plant at a first time point, and predict a first future state, wherein the first future state comprises predicted state information indicative of a future state of one or more processes of the synthetic fuel generation plant at a second time point subsequent the first time point. The system further comprises an optimisation unit in communication with the interface unit and the digital twin. The optimisation unit is configured to obtain an objective function which in use maps from a given state to an objective value for said given state. The objective value for the given state is indicative of an estimated quantity and/or quality of synthetic fuel generated by the one or more processes when the synthetic fuel generation plant is in the given state. The optimisation unit is further configured to perform an optimisation process to determine an updated state from the initial state. The optimisation process is operable to determine an initial future state for the initial state using the digital twin, wherein the initial future state comprises predicted state information indicative of the future state of one or more processes of the synthetic fuel generation plant at a future time point subsequent the initial time point. The optimisation process is further operable to optimise the objective function to obtain the updated state such that a first objective value determined by the objective function for an updated future state is greater than a second objective value determined by the objective function for the initial future state. The updated future state is determined from the updated state by the digital twin, and the updated future state comprises predicted state information indicative of the future state of one or more processes of the synthetic fuel generation plant at the future time point.

According to a further aspect of the present disclosure there is provided a computer-implemented method for optimising a fuel generation process performed by a synthetic fuel generation plant. The computer-implemented method comprises obtaining an initial state associated with the synthetic fuel generation plant, the initial state comprising state information indicative of a state of one or more processes of the synthetic fuel generation plant at an initial time point. The computer implemented method further comprises obtaining a digital twin representative of the synthetic fuel generation plant. The digital twin comprising a trained machine learning model which in use receives a first state associated with the synthetic fuel generation plant at a first time point, and predicts a first future state, wherein the first future state comprises predicted state information indicative of a future state of one or more processes of the synthetic fuel generation plant at a second time point subsequent the first time point. The computer-implemented method further comprises obtaining an objective function which in use maps from a given state to an objective value for said given state. The objective value for the given state is indicative of an estimated quantity and/or quality of synthetic fuel generated by the one or more processes when the synthetic fuel generation plant is in the given state. The computer-implemented method further comprises performing an optimisation process to determine an updated state from the initial state. The optimisation process comprises determining an initial future state for the initial state using the digital twin. The initial future state comprises predicted state information indicative of the future state of one or more processes of the synthetic fuel generation plant at a future time point subsequent the initial time point. The optimisation process further comprises optimising the objective function to obtain the updated state such that a first objective value determined by the objective function for an updated future state is greater than a second objective value determined by the objective function for the initial future state. The updated future state is determined from the updated state by the digital twin, and the updated future state comprises predicted state information indicative of the future state of one or more processes of the synthetic fuel generation plant at the future time point.

According to an additional aspect of the present disclosure there is provided a computer readable storage medium comprising one or more program instructions which, when executed by one or more processors, cause the one or more processors to perform a method for optimising a fuel generation process performed by a synthetic fuel generation plant. The method comprises obtaining an initial state associated with the synthetic fuel generation plant, the initial state comprising state information indicative of a state of one or more processes of the synthetic fuel generation plant at an initial time point. The method further comprises obtaining a digital twin representative of the synthetic fuel generation plant. The digital twin comprising a trained machine learning model which in use receives a first state associated with the synthetic fuel generation plant at a first time point, and predicts a first future state, wherein the first future state comprises predicted state information indicative of a future state of one or more processes of the synthetic fuel generation plant at a second time point subsequent the first time point. The method further comprises obtaining an objective function which in use maps from a given state to an objective value for said given state. The objective value for the given state is indicative of an estimated quantity and/or quality of synthetic fuel generated by the one or more processes when the synthetic fuel generation plant is in the given state. The method further comprises performing an optimisation process to determine an updated state from the initial state. The optimisation process comprises determining an initial future state for the initial state using the digital twin. The initial future state comprises predicted state information indicative of the future state of one or more processes of the synthetic fuel generation plant at a future time point subsequent the initial time point. The optimisation process further comprises optimising the objective function to obtain the updated state such that a first objective value determined by the objective function for an updated future state is greater than a second objective value determined by the objective function for the initial future state. The updated future state is determined from the updated state by the digital twin, and the updated future state comprises predicted state information indicative of the future state of one or more processes of the synthetic fuel generation plant at the future time point.

Beneficially, a synthetic fuel generation plant according to the present disclosure can be remotely operated to ensure that a high-quality and/or quantity of fuel is produced in an efficient, optimal, manner. The control processes of the synthetic fuel generation plant can be automatically and continuously monitored in order to optimise the fuel generation process. This ensures that the variables used in the plant are constantly refined such that a high-quality and/or quantity of fuel is consistently produced with minimal to no human intervention, while consumed energy is minimised and the other outputs remain in the predefined quality margins.

Optionally, but preferably, the control system further comprises an action unit configured to cause the synthetic fuel generation plant to transition to the updated state determined by the optimisation process.

Optionally, the action unit is further configured to determine an action plan to transition the synthetic fuel generation plant from the initial state to the updated state.

Optionally, in order to cause the synthetic fuel generation plant to transition to the updated state, the interface unit is further configured to provide the action plan to the synthetic fuel generation plant for execution by the synthetic fuel generation plant.

Optionally, the action plan comprises a command to control an actuator of the synthetic fuel generation plant, wherein the actuator is associated with a processes of the synthetic fuel generation plant.

Optionally, but preferably, the state information comprises a sensor value associated with a corresponding sensor of the synthetic fuel generation plant, wherein the sensor is associated with a process of the synthetic fuel generation plant.

Optionally, but preferably, the trained machine learning model is a supervised machine learning model trained on a dataset of historical states.

Beneficially, the use of machine learning allows for the complex parameterisation of a synthetic fuel generation plant to be modelled in order to determine optimal control procedures which lead to a high-quality and/or quantity of fuel being produced.

Optionally, the dataset of historical states is obtained from a plurality of fuel generation plants and relevant environmental data affecting the operation of the plant.

Optionally, the action unit is further configured to cause a remote synthetic fuel generation plant to transition to the updated state determined by the optimisation process.

Beneficially, efficient control procedures learnt in a first synthetic fuel generation plant can be applied to a second fuel generation plant in order to enable both synthetic fuel generation plants to operate efficiently and productively.

Optionally, the action unit is further configured to determine a remote action plan to transition the remote synthetic fuel generation plant to the updated state.

Optionally, the interface unit is further configured to be communicably coupled to the remote synthetic fuel generation plant. Optionally, in order to cause the remote synthetic fuel generation plant to transition to the updated state the interface unit is further configured to provide the action plan to the remote synthetic fuel generation plant for execution by the remote synthetic fuel generation plant.

Optionally, but preferably, optimisation of the objective function is constrained by a predefined constraint. Optionally, the predefined constraint in use restricts the possible values of the state information of the updated state.

Optionally, but preferably, the computer-implemented method further comprises causing the synthetic fuel generation plant to transition to the updated state determined by the optimisation process.

Optionally, the computer-implemented method further comprises determining an action plan to transition the synthetic fuel generation plant from the initial state to the updated state.

Optionally, causing the synthetic fuel generation plant to transition to the updated state comprises causing an execution of the action plan by the synthetic fuel generation plant.

Optionally, the computer-implemented method further comprises causing a remote synthetic fuel generation plant to transition to the updated state determined by the optimisation process.

Optionally, the computer-implemented method further comprises determining a remote action plan to transition the remote synthetic fuel generation plant to the updated state. Optionally, the computer-implemented method further comprises causing an execution of the action plan by the remote synthetic fuel generation plant.

Optionally, the computer readable storage medium is a non-transitory computer readable storage medium

BRIEF DESCRIPTION OF DRAWINGS

Embodiments of the invention will now be described, by way of example only, and with reference to the accompanying drawings, in which.

DETAILED DESCRIPTION

Embodiments of the present disclosure will be now described with reference to the attached figures. It is to be noted that the following description is merely used for enabling the skilled person to understand the present disclosure, without any intention to limit the applicability of the present disclosure to other embodiments which could be readily understood and/or envisaged by the reader. In particular, whilst the present disclosure is primarily directed to the optimisation of a fuel generation process performed by a synthetic fuel generation plant, the skilled person will appreciate that the systems and methods described herein are applicable to the automation and optimisation of other plant processes.

Figure 1:
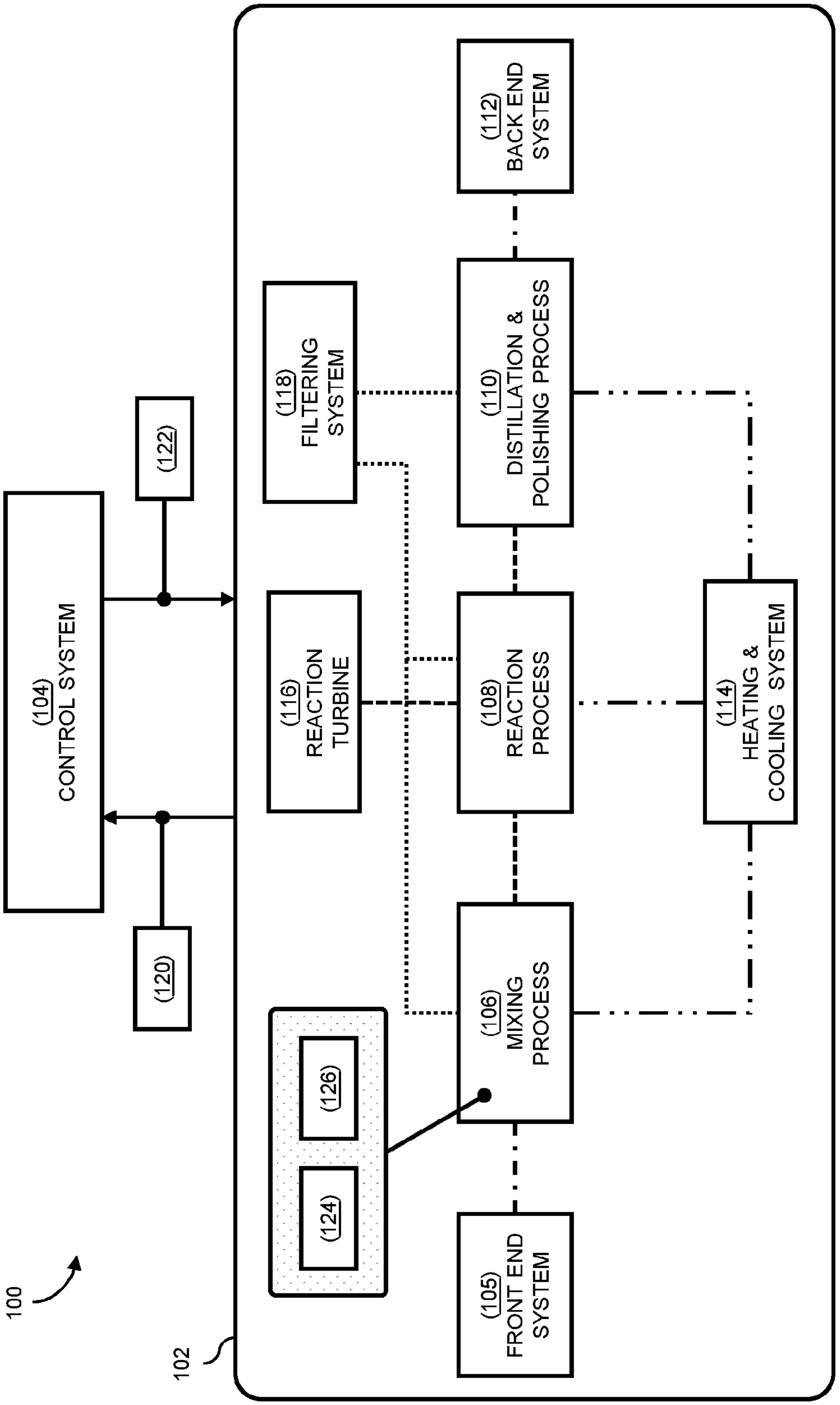
FIG. 1 shows a synthetic fuel generation system according to one embodiment.

FIG. 1 shows synthetic fuel generation system 100 according to one embodiment.

Synthetic fuel generation system 100 comprises synthetic fuel generation plant 102 and control system 104 communicatively coupled to synthetic fuel generation plant 102. Synthetic fuel generation plant 102 comprises front end system 105, mixing process 106, reaction process 108, distillation process 110, and back end system 112. As such, synthetic fuel generation plant 102 comprises a fuel generation process involving plurality of processes 106, 108, 110. Synthetic fuel generation plant 102 further comprises heating and cooling system 114, reaction turbine 116, and filtering system 118.

Synthetic fuel generation plant 102 transforms any properly prepared hydrocarbon material into a high-quality synthetic fuel through a low temperature and low pressure chemical process, such as the Catalytic Depolymerisation Process (CDP). Synthetic fuel generation plant 102 mimics the natural process of transforming organic waste and plastic to synthetic fuel. The main difference is the time reduction of the natural transformation process from more than 300 million years to less than 10 minutes by using crystalline catalysts (e.g., Cation-Aluminium-Silicate), at the temperature of approximately 240° C. to 320° C., and mixing and warming up the feedstock with the catalyst in a carrier fluid, preferably oil with a turbine. Such chemical processes are known in the art, and any suitable process may be used. Furthermore, the physical aspects of the synthetic fuel generation plant 102 are also known in the art.

Input materials, or feedstock, are fed through front end system 105 into mixing process 106. The flow of material between front end system 105 and mixing process 106 is a batch material flow, one batch is one type of input materials, as indicated by the first line style connecting front end system 105 to mixing process 106 in FIG. 1. The input materials are preferably prepared, dried, and shredded by front end system 105 prior to being fed into mixing process 106. Mixing process 106 feeds the input materials into warmed up process oil from heating system 114 and mixes with a catalyst and lime for further processing. The mixture is preferably heated to between 180° C. to 220° C. Heat oil flow is indicated in FIG. 1 by the second line style, as shown by the line connecting heating system 114 to mixing process 106. During mixing process 106, the input material decomposes, and water evaporated from the input material is fed through a distillation column (not shown).

The mixed and decomposed mixture from mixing process 106 is fed to reaction process 108 where the mixture is further processed in reaction turbine 116 to form a synthetic fuel steam and/or foam. The flow of material between mixing process 106 and reaction process 108 is a continuous material flow, as indicated by the third line style connecting mixing process 106 to reaction process 108 in FIG. 1. The evaporated synthetic fuel is distilled within reaction process 108 through a first fuel distillation column (not shown). Sludge produced as a result of reaction process 108 is exported via filtering system 118. Sludge flow is indicated in FIG. 1 by the fourth line style, as shown by the line connecting reaction process 108 to filtering system 118 in FIG. 1.

The raw synthetic fuel produced in reaction process 108 is fed to distillation process 110 to redistill into a synthetic fuel that can be directly used in internal combustion engines. The flow of material between reaction process 108 and distillation process 110 is a continuous material flow. Preferably, the raw synthetic fuel is heated to approximately 320° C. for the final distillation and filtration in order to reach the final fuel quality. The resulting synthetic fuel is then fed to back end system 112 for storage. The flow of material between distillation process 110 and back end system 112 is a batch material flow. In case of emergency, process materials and fluids used in plant processes 106, 108, 110 can be drained into a spare tank (not shown).

Synthetic fuel generation plant 102 is controlled by control system 104. In an embodiment, the control system forms a part of the synthetic fuel generation plant and is co-located with the synthetic fuel generation plant. In an alternative embodiment, the control system is remote to the synthetic fuel generation plant such that the synthetic fuel generation plant is remotely operated by the control system via a network. Sensor readings 120 from plant processes of synthetic fuel generation plant 102 are received by control system 104, and actuator signals 122 are sent from control system 104 to plant processes 102. As described in more detail below, sensor readings 120 are obtained from a plurality of sensors monitoring synthetic fuel generation plant 102, such as sensor 124 associated with mixing process 106. Actuator signals 122 control one or more actuators used to synthetic fuel generation plant 102, such as actuator 126 associated with mixing process 106. Accordingly, synthetic fuel generation plant 102 comprises a plurality of sensors and a plurality of actuators. The plurality of sensors is operable to monitor the state of synthetic fuel generation plant 102. The plurality of actuators are operable to affect the state of synthetic fuel generation plant 102. Therefore, the sensors and actuators of a synthetic fuel generation plant are operable to monitor and control the core process parameters of the synthetic fuel generation plant.

According to an aspect of the present disclosure, control system 104 is operable to optimise the synthetic fuel generation process performed by synthetic fuel generation plant 102. In an embodiment, control system 104 learns the core process parameters of synthetic fuel generation plant 102 and provides control procedures which optimise the quality and/or quantity of the synthetic fuel generated whilst reducing the overall energy consumption. Synthetic fuel generation system 100 is therefore able to operate without human intervention and can be controlled remotely. Beneficially, this allows for a high quality and/or quantity of synthetic fuel to be generated in an efficient way without requiring continuous human interaction. Furthermore, the use of the synthetic fuel generation system 100 allows for optimisation of control parameters during use. Control system 104 is able to optimise the fuel generation process continuously thereby ensuring that synthetic fuel generation plant 102 is operating in a resource efficient manner. Furthermore, a network of different synthetic fuel generation plants can be monitored and remotely optimised in order to ensure that the quality and/or quantity of fuel generated across the network is optimal.

Figure 2:
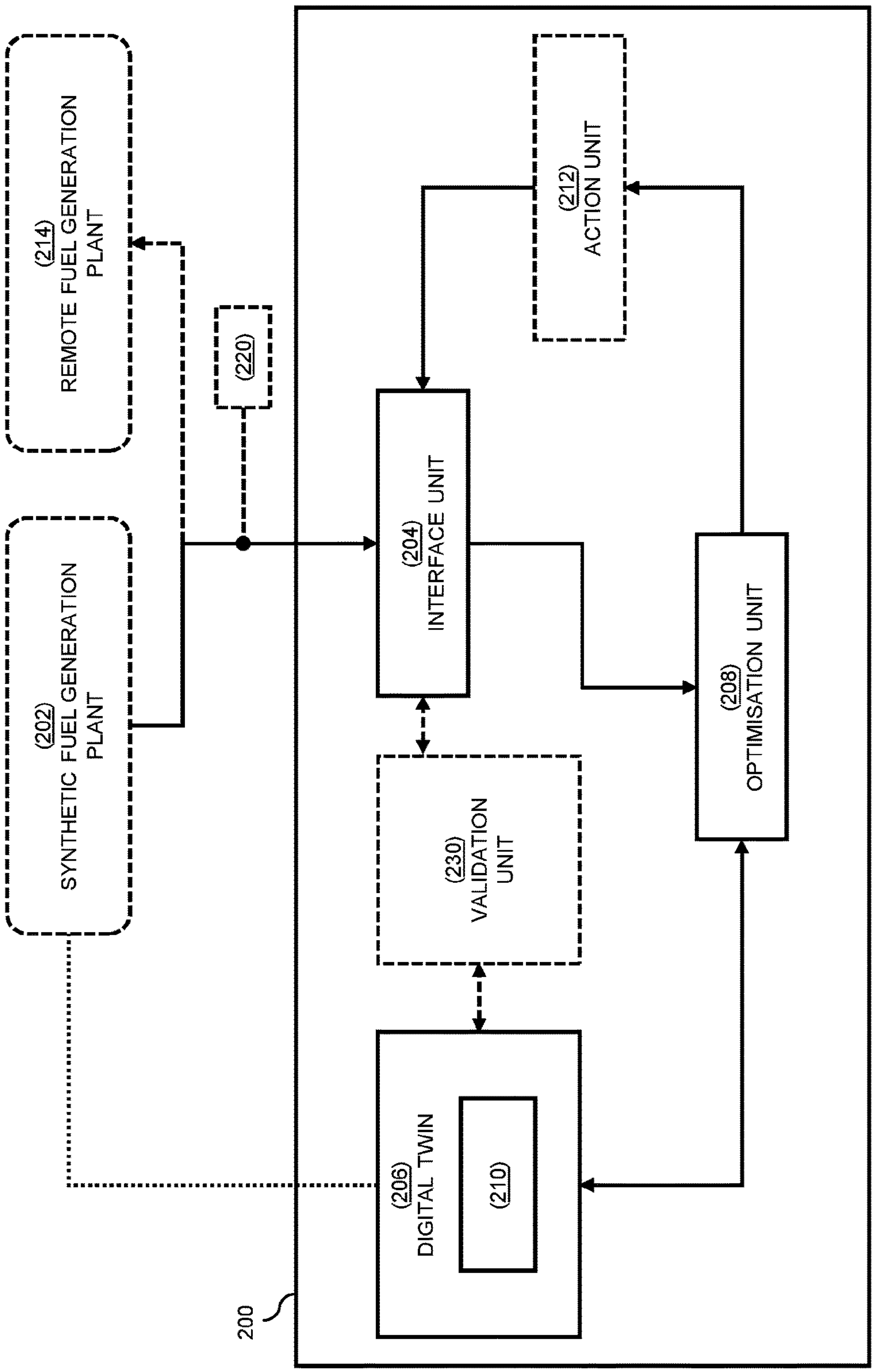
FIG. 2 shows a control system according to an aspect of the present disclosure.

FIG. 2 shows control system 200, which is an embodiment of control system 104 of FIG. 1, according to an aspect of the present disclosure.

Control system 200 optimises a fuel generation process performed by synthetic fuel generation plant 202, which corresponds to an embodiment of synthetic fuel generation plant 102 shown in FIG. 1. Control system 200 comprises interface unit 204, digital twin 206, and optimisation unit 208. Optionally, control system 200 further comprises data processing module 220 and validation unit 230.

In general, control system 200 optimises the fuel generation process performed by synthetic fuel generation plant 202 by searching for an updated state of synthetic fuel generation plant 202 which is predicted to produce synthetic fuel having one or more desirable characteristics. Example characteristics include high fuel quality, high fuel quantity, and stability. A further desirable characteristic can be a low energy consumption of the synthetic fuel generation process. In order to predict the state of synthetic fuel generation plant 202 at a future time point, digital twin 206 is operable to determine a predicted future state of synthetic fuel generation plant 202 from a given state. An objective function is then used to quantify the characteristics—e.g., quantity and/or quality—of the synthetic fuel produced when synthetic fuel generation plant 202 is in the predicted future state. Therefore, optimisation unit 208 searches, from the initial state of synthetic fuel generation plant 202, for an updated state which is predicted by digital twin 206 and the objective function to lead to synthetic fuel being produced with optimal characteristics. Optionally, validation unit 230 adds context and reasoning to updated states predicted by digital twin 206, and interfaces with interface unit 204 and digital twin 206.

Control system 200 is configured to monitor synthetic fuel generation plant 202 and learn the most effective state for synthetic fuel generation plant 202 to produce a high quality and/or quantity of fuel. Beneficially, this optimisation procedure is performed without the need for human intervention and leads to a more efficient fuel generation process which makes more efficient use of the feedstock to improve the quality and/or quantity of fuel produced.

Control system 200 can be implemented on a computing device (as described in relation to FIG. 6 below), or across a network of computing devices, with functional units split across the network in a known manner. In an embodiment, the control system is implemented as software executing on a computing device or a network of computing devices. In an alternative embodiment, the control system is implemented in hardware, or is implemented in both hardware and software.

In order to determine the current state of synthetic fuel generation plant 202, interface unit 204 is configured to be communicably coupled to synthetic fuel generation plant 202. Preferably, interface unit 204 is communicatively coupled to a network interface (not shown) such that communications are received and sent by means of a network accessible via the network interface. In one embodiment, the network is a local area network. In an alternative embodiment, the network is a wide area network. Preferably, interface unit 204 is configured to encrypt all communications sent from control system 200 to a synthetic fuel generation plant, such as synthetic fuel generation plant 202, and is further configured to decrypt all communications received from a synthetic fuel generation plant. In an embodiment where the control system is co-located with the synthetic fuel generation plant, the control system is connected to the synthetic fuel generation plant by means of a dedicated network utilising preferably the Sidenet security protocols.

Interface unit 204 is operable to obtain an initial state associated with synthetic fuel generation plant 202. The initial state comprises state information indicative of a state of one or more processes of synthetic fuel generation plant 202 at an initial time point. For example, the initial state can comprise state information indicative of the state of the mixing process, reaction process, and/or distillation process of the synthetic fuel generation plant. In an embodiment, interface unit 204 is operable to obtain a stream of states from synthetic fuel generation plant 202, wherein a state is received after a predetermined period of time has elapsed.

Generally, state information provides a snapshot of the synthetic fuel generation process performed by a synthetic fuel generation plant at a given timepoint. As such state information preferably comprises a measurement value and a timestamp. Preferably, the state information comprises a sensor value, or measurement, associated with a corresponding sensor of synthetic fuel generation plant 202 at a given timepoint. The sensor is associated with a process of synthetic fuel generation plant 202. More preferably, the state information comprises a plurality of sensor values, or measurements, associated with a corresponding plurality of sensors and/or actuators of synthetic fuel generation plant 202. The plurality of sensors and/or actuators are associated with the fuel generation processes performed by a synthetic fuel generation plant (e.g., mixing process 106, reaction process 108, and/or distillation process 110 shown in FIG. 1).

Example measurements (i.e., sensor values and/or actuator values) included in the state information include: temperature in the distillation tank, temperature in the evaporating column, screw conveyer speed in the front end system, fuel temperature after separation, water steam temperature after separation, flashpoint of a specific process (e.g., the reaction process), cetane number of a specific process (e.g., the reaction process), and cetane index (e.g., the reaction process). The foregoing list is intended to be illustrative and not exhaustive, as illustrated by the further examples provided with reference to FIG. 3 below. In an exemplary embodiment of the present disclosure, the state information is obtained from up to 170 different sensors within the synthetic fuel generation plant.

Sensor values, or measurements, within the state information can be real valued, or Boolean valued. Preferably, the range of possible values for each sensor and/or actuator within a synthetic fuel generation plant is bounded such that each sensor value or measurement is likewise bounded.

In one embodiment, state information is received from synthetic fuel generation plant 202 after a predetermined period of time has elapsed from the previous receipt of state information. Preferably, the predetermined period of time is at least 5 seconds and is at most one hour. More preferably, the predetermined period of time is between 10 to 15 minutes. In one embodiment, the state information comprises all possible sensor values, or measurements. Alternatively, the state information comprises only a subset of possible sensor values, or measurements. In an embodiment, each sensor and/or actuator comprises a sampling rate such that the state information for more important sensors and/or actuators is received more frequently than the state information for less important sensors and/or actuators. Optionally, any sensor values missing from state information within a received state can be estimated using previous sensor values (e.g., by means of regression analysis or interpolation).

In an embodiment, state information received by interface unit 204 from synthetic fuel generation plant 202 is automatically cleaned and/or pre-processed prior to being sent to other units of control system 200. Optionally, automated cleaning and processing of information is performed by data transformation module 220. Further detail on data transformation module 220 is provided in the description of FIG. 8.

Optionally, the state information is pre-processed in order to identify any outlier values related to wrong sensor readings, defects appearing as a result of communication (i.e., noise), wrong manual inputs, etc. Anomaly detection can be performed using any known approach such as density-based techniques, cluster analysis, fuzzy logic-based outlier detection, and one-class support vector machines. In one embodiment, values identified as outliers are removed from the state information. Alternatively, values identified as outliers can be flagged for review by a human operator, such that the human operator can determine whether or not to remove or maintain the predicted outlier value.

Optionally, the state information or the pre-processed state information is cleaned using an active learning approach. Active learning is a subset of machine learning whereby a machine learning algorithm can query a human in order to provide further information regarding state values. Such techniques are known in the art. In the present embodiment, active learning is used to provide an automatic classification model that is able to classify state values into a normal class and a suspicious class. In particular, active learning is used to identify edge cases for which the machine is not entirely clear how to classify. The received human decision is integrate into the learned model in order to minimise the workload of manually labelling all examples.

Initially, active learning is used to clean historical state information received from a synthetic fuel generation plant thereby to determine a cleaning model. A dialog based on active learning with a Support Vector Machine (SVM) enabled balanced sampling is used. The active learning algorithm results in an optimal sampling of the list of pairs for maximal information gain about the given classifier induction problem.

Once the cleaning model has been learnt, and during operation of control system 200, the cleaning model is combined with an additional ranking of the new state information values that are deemed suspicious. The additional ranking is preferably performed using a clustering based approach such as k-means clustering or hierarchical clustering. As such, the human expert need only answer the most informative examples as deemed by the ranking.

Once the initial state information has been received by interface unit 204 and optionally cleaned/pre-processed, the initial state information is used by optimisation unit 208 and digital twin 206 to determine an updated state for synthetic fuel generation plant 202 which substantially optimises the synthetic fuel generation process, i.e., the updated state leads to a high-quality and/or quantity of fuel being produced.

Digital twin 206 is representative of synthetic fuel generation plant 202. As such, digital twin 206 may be considered a digital representation of synthetic fuel generation plant 202, or a digital model of the processes of synthetic fuel generation plant 202. A digital twin can therefore be used to model the behaviour of a synthetic fuel generation plant over a period of time in order to determine the relationship between the core process parameters, or state of the, state of the synthetic fuel generation plant environment, input materials, and the fuel and other outputs subsequently produced.

Digital twin 206 comprises trained machine learning model 210 configured to receive a first state associated with synthetic fuel generation plant 202 at a first time point.

Trained machine learning model 210 is further configured to predict a first future state. The first future state comprises predicted state information indicative of a future state of one or more processes of synthetic fuel generation plant 202 at a second time point subsequent the first time point.

Preferably, trained machine learning model 210 is a supervised machine learning model trained on a dataset of historical states. Examples of supervised machine learning models include, but are not limited to, Support Vector Machines (SVMs), multilayer perceptrons, naïve Bayes, genetic programming, and nearest neighbour algorithms. The skilled person will appreciate that the machine learning model can be trained using any standard approach. In an example embodiment, the dataset of historical states is split into a training set, validation set, and test set. Preferably, the training and validation sets comprise 80% of the dataset of historical states and the test set comprises 20% of the dataset of historical states. The training set preferably comprises 80% of the training and validation sets and the validation set preferably comprises 20% of the training and validation sets. Optionally, hyperparameter optimisation can be performed using any known technique such as grid search, evolutionary optimisation, or Bayesian optimisation.

The machine learning model is trained to predict the state of the fuel generation plant at a predetermined timepoint in the future. Preferably, the predetermined time point corresponds to between 5 seconds in the future and 1 hour in the future. More preferably, the predetermined time point corresponds to 10 to 15 minutes in the future. As such, when training the machine learning model on a dataset of historical states, an input to the machine learning model comprises a state of a synthetic fuel generation plant at time point t, and the target to be predicted comprises a state of the synthetic fuel generation plant at time point t+n, where n is a value fixed during training.

In one embodiment, the dataset of historical states is obtained from a plurality of fuel generation plants. In an alternative embodiment, the dataset of historical states is obtained only from synthetic fuel generation plant 202. Optionally, the dataset of historical states is pre-processed and/or cleaned according to the active learning method described above.

In an exemplary embodiment of the present disclosure, the machine learning model utilised by the digital twin was trained on a training dataset comprising state information received from a synthetic fuel generation plant over an 18 month period. The training dataset comprised 7,000 hours of plant operation with state information comprising measurements from up to 170 sensors included within the synthetic fuel generation plant. The training data set included 4,200 hours of continuous operation (i.e., operation 24 hours a day, 7 days a week), and 2,800 hours of failures and idle time. When using active learning to clean the data, 128 cases were provided to the expert for further analysis, with the rest of the data automatically cleaned with an error detection accuracy of 97%.

The training and application of trained machine learning model 210 is detailed as a non-limiting example of an embodiment. The data for trained machine learning model 210 comprises data libraries of multiple layered data ontologies as described in FIG. 7 below, which may have been processed using methods of FIG. 7, FIG. 8, FIG. 9, or FIG. 10. The data may include manually produced data; synthetic data; data collected through manual processes; data collected through semi-automatic process; data collected through fully automatic processes; automated manually labelled data; or automated or manually clustered data. In this example, the data has been enriched with contextual information through contextual mapping, as described in FIG. 8 below. Examples within a data ontology for chemical processes include manually labelled and produced information from knowledge bases on chemical reactions, and information on chemical reactions collected and grouped using web mining techniques known in the field, which is then enriched with contextual data such as the future supply of necessary reagents to the plant. Additional relevant data is added to the data libraries to generate a larger dataset for training through suitable data augmentation methods known in the field in combination with data mining methods described in FIG. 7. Augmentation methods can include back translation, AutoAugment, and TF-IDF word replacement. Management of data libraries is semi-automated, with automated data segmentation through suitable clustering algorithms and monitoring by human experts. The core machine learning module is a supervised SVM algorithm, making use of all labelled data in the data libraries, and trained using any standard method known in the field including, for example back propagation, cascade training and parallel training. The trained model input is multimodal data including the current information from the plant (such as data from sensors over the last 10 minute window) and contextually relevant information from data libraries. The output is then a predicted future state, such as predicted sensor readings 10 minutes into the future, including predicted output from the plant. In application, this results in the transformation of data on the current and past state of the plant into a predicted future state.

Trained machine learning model 210 of digital twin 206 is utilised by optimisation unit 208 in order to find a state for synthetic fuel generation plant 202 which is predicted to lead to a high-quality and/or quantity of fuel being produced.

In order to determine the predicted quality and/or quantity of fuel, optimisation unit 208 is configured to obtain an objective function which in use maps from a given state to an objective value for said given state. Particularly, the objective function in use maps from a predicted future state, obtained using digital twin 206, to an objective value for the predicted future state. The objective value for a given state is indicative of an estimated quantity and/or quality of synthetic fuel generated by the one or more processes of synthetic fuel generation plant 202 when synthetic fuel generation plant 202 is in the given state. As such, whilst the input to the optimisation process is a state of a fuel generation plant at time point t, the optimisation process predicts the quality and/or quantity of the fuel generated at a time point t+n.

In an embodiment, the state information provided to digital twin 206 and optimisation unit 208 is supplemented with data indicative of environmental and/or external factors. Examples of such data include the temperature of the outside environment within which synthetic fuel generation plant 202 resides, the humidity of the outside environment within which synthetic fuel generation plant 202 resides, and the current dust particle levels. In this embodiment, the supplemental data is also used when training the machine learning model of digital twin 206.

Optimisation unit 208 is configured to perform an optimisation process to determine an updated state from the initial state. The optimisation process is operable to determine an initial future state for the initial state using digital twin 206. The initial future state comprises predicted state information indicative of the future state of one or more processes of synthetic fuel generation plant 202 at a future time point subsequent the time point of the initial state. The optimisation process is further operable to optimise the objective function to obtain the updated state such that a first objective value determined by the objective function for an updated future state is greater than a second objective value determined by the objective function for the initial future state. The updated future state is determined from the updated state by digital twin 206. The updated future state comprises predicted state information indicative of the future state of one or more processes of synthetic fuel generation plant 202 at the future time point.

As such, the goal of the optimisation process performed by optimisation unit 208 is to search for a state of synthetic fuel generation plant 202 which is predicted to lead to the generation of optimal or near optimal synthetic fuel in the future, where optimality is defined by an objective function (as described in more detail below).

Optionally, the validation unit 230 interfaces with one or both of the digital twin 206, and interface unit 204. Validation unit 230 receives updated state information from digital twin 206 for further analysis and processing, which may include independent chemical and non-chemical analysis, feature extraction, data formalisation, and other relevant processes to aid quantitative and qualitative synthetic fuel cell generation evaluation, such as interactive visualisations. Further detail on validation unit 230 is provided below with reference to FIG. 7. As described with reference to FIG. 7 the validation unit provides a human understandable output in response to a query made to the system. Such an output enables an operator of the system to understand, and have confidence in, the decisions made by the system.

Figure 3:
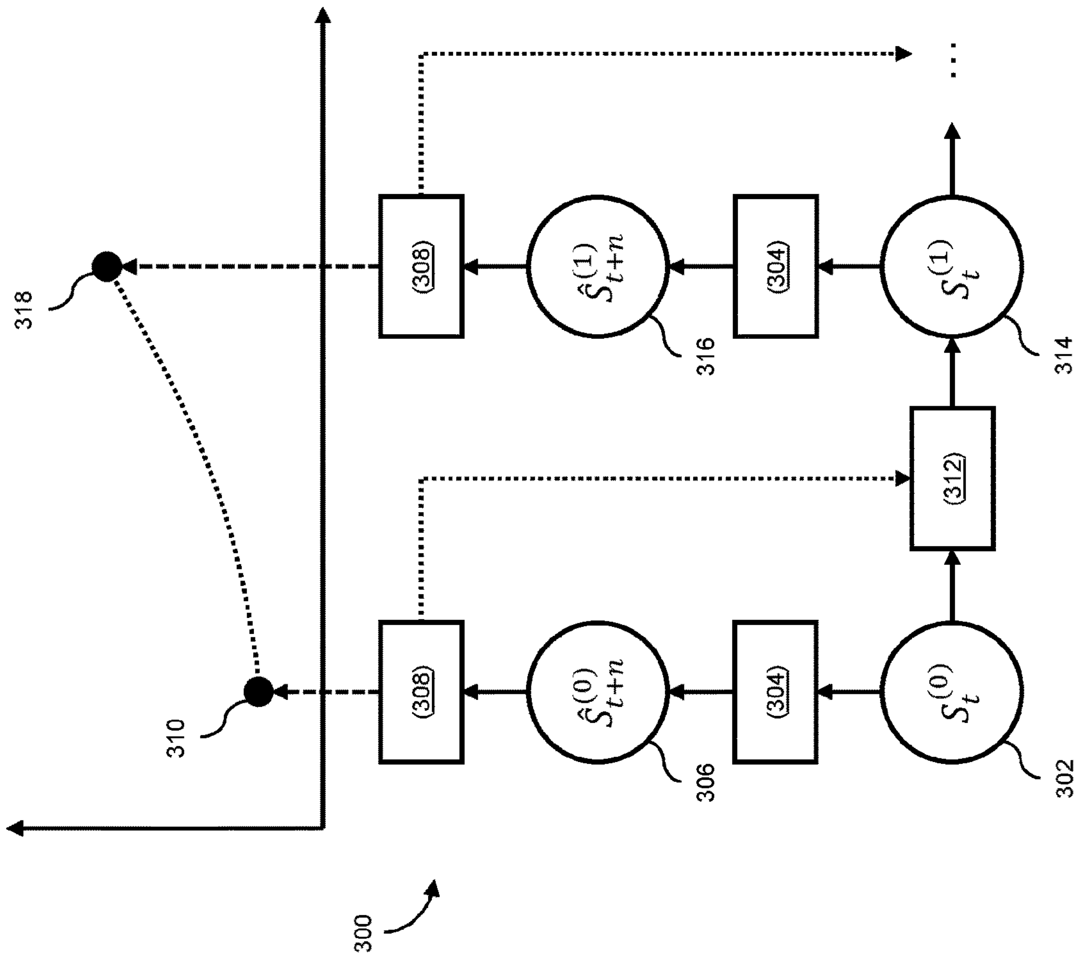
FIG. 3 illustrates an optimisation process according to an aspect of the present disclosure.

FIG. 3 illustrates the optimisation process performed by optimisation unit 208 according to an aspect of the present disclosure.

FIG. 3 shows optimisation process 300 involving first state 302, digital twin 304, first future state 306, objective function 308, and first objective value 310. First state 302 corresponds to an initial state of a synthetic fuel generation plant at a first time point. First future state 306 is determined from first state 302 by digital twin 304. First future state 306 corresponds to the predicted state of the synthetic fuel generation plant at a second, future, time point given that the synthetic fuel generation plant is in first state 302 at the first time point.

First objective value 310 is determined from first future state 306 by objective function 308. First objective value 310 corresponds to the estimated quality and/or quantity of the fuel generated by the synthetic fuel generation plant when the synthetic fuel generation plant is in first future state 306. As such, first objective value 310 represents the predicted future quality and/or quantity of the fuel at time point t+n given the synthetic fuel generation plant is in first state 302 at time point t.

Generally, an optimisation process performed by an optimisation unit, such as optimisation unit 208 of FIG. 2, searches for a target state of a synthetic fuel generation plant at a first time point, t, which is predicted to lead to high quality and/or quantity fuel being generated at a second time point t+n. Therefore, transitioning the synthetic fuel generation plant to the target state results in an optimisation of the fuel generation process performed by the synthetic fuel generation plant. This optimisation process can be repeatedly performed over time in order to maintain optimal or near optimal fuel generation. The repeated optimisation process can be performed in an efficient manner due to the computational efficiency of utilising a digital twin comprising a trained machine learning model to model the core process parameters of the synthetic fuel generation plant.

The optimisation process is illustrated in FIG. 3 which further shows optimisation step 312, second state 314, second future state 316, and second objective value 318. Optimisation step 312 determines second state 314 from first state 302 and objective function 308. That is, optimisation step 312 finds second state 314 as a result of an optimisation of objective function 308 given first state 302. In the example shown in FIG. 3, optimisation step 312 seeks to maximise objective function 308 to determine second state 314. Accordingly, second state 314 corresponds to the updated state produced as a result of performing an optimisation.

Second future state 316 is predicted from second state 314 by digital twin 304. Second future state 316 is estimated to have second objective value 318 which is greater than first objective value 310. Therefore, when the synthetic fuel generation plant is in second state 314 it is predicted to produce a higher quality and/or quantity of fuel than when the synthetic fuel generation plant is in first state 302.

In consequence, changing the state of the synthetic fuel generation plant from first state 302 to second state 314 result in an improvement in the quality and/or quantity of the fuel generated by the synthetic fuel generation plant as measured by objective function 308. As such, a digital model of the synthetic fuel generation plant can be used to identify an optimal state for the synthetic fuel generation plant in an efficient way.

Generally, an objective function, such as objective function 308, takes an input state and determines an objective value indicative of the quality and/or quantity of fuel generated when a synthetic fuel generation plant is in the input state. The quality and/or quantity of fuel generated is determined from one or more measurement values of the input state.

As stated above, a state provides a snapshot of the synthetic fuel generation process performed by a synthetic fuel generation plant at a given timepoint. Preferably, a state comprises a sensor value, or measurement, associated with a corresponding sensor of a synthetic fuel generation plant at a given timepoint. The sensor is associated with a process of the synthetic fuel generation plant (e.g., the mixing process, reaction process, and or distillation process). The values included in a state at time point t can thus be used to determine the quality and/or quantity of fuel generated by the fuel generation plant at the time point t.

In an embodiment, an objective function, such as objective function 308 of FIG. 3, maps from an input state to an objective value based on a comparison of the input state to an optimal state. The optimal state is a predetermined state which is associated with a high quality and/or quantity of fuel. That is, the optimal state includes one or more values of a fuel generation plant which indicate a high quality and/or quantity of fuel is being generated by the fuel generation plant. Preferably, the objective function is similarity-based such that an objective value produced by the objective function corresponds to a degree of similarity between an input state and an optimal state. In this instance, an optimisation process seeks to maximise the objective function thus maximising the similarity between the input state and the optimal state. Alternatively, the objective function is difference-based such that an objective value produced by the objective function corresponds to a degree of difference between an input state and an optimal state. In this instance, an optimisation process seeks to minimise the objective function thus minimising the difference between the input state and the optimal state.

In one embodiment, the optimal state used by an objective function, such as objective function 308 of FIG. 3, corresponds to a high quality of raw fuel coming out of the reaction process, such as reaction process 108 shown in FIG. 1. Accordingly, transitioning a synthetic fuel generation plant to a state identified by an optimisation process as leading to a future state approximating the optimal state will result in the synthetic fuel generation plant improving the quality of raw fuel coming out of the reaction process.

The synthetic fuel produced as a result of the fuel generation process after the first distillation and filtration (occurring during the reaction process) has a so-called "raw diesel" quality. The quality parameters are therefore lower compared to the final fuel quality but indicate the base for further quality treatment to reach high-quality synthetic fuel. In practice, this synthetic fuel can be for example used for electricity generation in modern internal combustion electricity generators or for long time storing of liquid energy.

In this embodiment, the optimal state comprises a plurality of measurements associated with the processes of the synthetic fuel generation plant. The measurements relate to sensor values received from sensors monitoring the reaction process and include the cetane number, the cetane index, the density (at 15° C.), the flash point, the sulphur content, and the colour of the fuel coming from the reaction process. Preferably, the optimal state defines the optimal cetane number as being from 50 to 55, the optimal cetane index as being from 45 to 50, the optimal density (at 15° C.) as being from 820 to 860, the optimal flash point as being from 40° C. to 50° C., the optimal sulphur content as being the same as in the feedstock, and the optimal colour as dark brown and turbid. In an embodiment, the preferable ranges are used as constraints to the optimisation process.

In this embodiment, the objective function compares a future state, determined by a digital twin, to the optimal state in order to estimate the quality of raw fuel coming out of the reaction process at a time point t+n given the synthetic fuel generation plant is in an initial state at time point t. As such, the optimisation process searches for a state which results in a future state comprising optimal values for the cetane number, the cetane index, the density (at 15° C.), the flash point, the sulphur content, and the colour of the fuel coming from the reaction process.

Additionally, or alternatively, the optimal state used by an objective function, such as objective function 308 of FIG. 3, corresponds to a stable production of quality synthetic fuel with minimal energy consumption. Accordingly, transitioning a synthetic fuel generation plant to a state identified by an optimisation process as leading to a future state approximating the optimal state will result in the synthetic fuel generation plant achieving stable and potentially higher production of quality synthetic fuel with minimal energy consumption.

In this embodiment, the synthetic fuel produced in the optimal state after the second distillation column or after passing the filtration system (depending on fuel characteristics) meets 90-95% of the EN590 standard for diesel fuel. Some minor characteristics may vary due to feedstock specifics and are adjusted during further refinement (polishing) of the produced fuel. The synthetic-bio diesel after the second distillation or filtration system can be used for electricity generation, long term energy storage in form of liquid fuel or used in transportation in any modern diesel engine (e.g., cars, trucks, busses, agricultural machinery, etc.).

In this embodiment, the optimal state comprises a plurality of measurements associated with the processes of the synthetic fuel generation plant. The measurements relate to sensor values received from sensors monitoring the reaction process and include the cetane number, the cetane index, the density (at 15° C.), the flash point, the sulphur content, and the colour of the fuel coming from the reaction process. Preferably, the optimal state defines the optimal centane number as being from 50 to 55, the optimal cetane index as being from 45 to 50, the optimal density (at 15° C.) as being from 840 to 850, the optimal flash point as being greater than 50° C., the optimal sulphur content as being less than 10 mg/kg, and the optimal colour as being light yellow and clear. In an embodiment, the preferable ranges are used as constraints to the optimisation process.

Preferably, the measurements in this embodiment further include the $CO_2$ produced. $CO_2$ is a regular by-product of the synthetic fuel generation plants. As such it is produced as a result of free carbon and oxygen molecules in form of $CO_2$. The amount of the $CO_2$ is directly correlated with the calorific value of the processed input materials, but the quality of the $CO_2$ is always the same range. The purity of the $CO_2$ is expressed in values that concentrations of other gasses, with the optimal state of the present embodiment defining the optimal values as being below detection limit.

Preferably, the measurements in this embodiment further include the quantity of the sludge produced (e.g., as measured by a filtering system, such as filtering system 118 of FIG. 1). The optimal state of the present embodiment defines the optimal quantity of sludge produced is preferably less than and including 15% of the input material and more preferably less than and including 10% of the input material.

Preferably, the measurements in this embodiment further include the quantity of water generated by the fuel generation processes, such as mixing process 106, reaction process 108, and distillation process 110 shown in FIG. 1. The optimal state of the present embodiment defines the optimal quantity of water generated by the fuel generation processes is preferably minimal but less than and including 15% of the input material.

Preferably, the measurements in this embodiment further include the total energy consumption. The optimal state of the present embodiment defines the optimal total energy consumption as being from 300 to 500 kWh for a medium size plant.

In this embodiment, the optimisation process searches for a state which results in a future state achieving stable and potentially higher production of quality synthetic fuel with minimal energy consumption as measured using the cetane number, the cetane index, the density (at 15° C.), the flash point, the sulphur content, and the colour of the fuel.

Whilst two optimal states are described above, the skilled person will appreciate that further optimal states are conceivable in order to ensure that a synthetic fuel generation plant produces a high-quality and/or quantity of fuel in an efficient manner. Indeed, a synthetic fuel generation plant can be remotely and efficiently configured to change the type of fuel generated by altering the optimal state. Furthermore, a centralised database of optimal states can be maintained and updated in order to control the operation of multiple synthetic fuel generation plants efficiently.

The above described optimisation processes can be performed by any suitable optimisation algorithm or approach. Example optimisation algorithms or approaches include, but are not limited to, Difference Approximations, Discretization Methods, Gradient Projection Methods, Homotopy Methods, Karush-Kuhn-Tucker (KKT) Reduction Methods, Nonlinear Simplex Methods, complex constraint logic programming methods, and forward chain reasoning.

With reference once again to FIG. 2, optimisation of the objective function performed by optimisation unit 208 in one embodiment is constrained by a predefined constraint. The predefined constraint in use restricts the possible values of the state information of the updated state. For example, if the state information comprises a value associated with a sensor of the synthetic fuel generation plant, then a constraint can be placed on the optimisation process to restrict the range of the value to the range of possible values of the sensor.

As stated previously, optimisation unit 208 is configured to determine an updated state from an initial state of the synthetic fuel generation plant such that the updated state is predicted to produce a high quality and/or quantity of synthetic fuel. In an embodiment, control system 200 further comprises action unit 212 configured to cause synthetic fuel generation plant 202 to transition to the updated state determined by the optimisation process performed by optimisation unit 208.

Preferably, action unit 212 is configured to determine an action plan to transition synthetic fuel generation plant 202 from the initial state to the updated state. In an embodiment, the action plan comprises a sequence of instructions which, when executed by synthetic fuel generation plant 202, cause synthetic fuel generation plant 202 to transition to the updated state. As such, the action plan optionally comprises a command to control an actuator of synthetic fuel generation plant 202, wherein the actuator is associated with a processes of synthetic fuel generation plant 202. For example, if the updated state comprises a first value associated with a temperature sensor, then the action plan comprises a command to control an actuator of the synthetic fuel generation plant associated with the temperature sensor in order to increase or reduce the temperature to the first value.

In an alternative embodiment, the action plan comprises the updated state and a corresponding control signal or instruction which indicates that the synthetic fuel generation plant is to transition to the updated state. In this embodiment, the operations required to transition the synthetic fuel generation plant to the updated state are determined by the synthetic fuel generation plant.

Preferably, in order to cause synthetic fuel generation plant 202 to transition to the updated state, interface unit 204 is further configured to provide the action plan to synthetic fuel generation plant 202 for execution by synthetic fuel generation plant 202.

In an embodiment, interface unit 204 is further configured to be communicably coupled to remote synthetic fuel generation plant 214. In this embodiment, action unit 212 is further configured to cause remote synthetic fuel generation plant 214 to transition to the updated state determined by the optimisation process performed by optimisation unit 208. Preferably, action unit 212 is further configured to determine a remote action plan to transition remote synthetic fuel generation plant 214 to the updated state.

In this embodiment, in order to cause remote synthetic fuel generation plant 214 to transition to the updated state interface unit 204 is further configured to provide the action plan to remote synthetic fuel generation plant 214 for execution by remote synthetic fuel generation plant 214.

Figure 4:
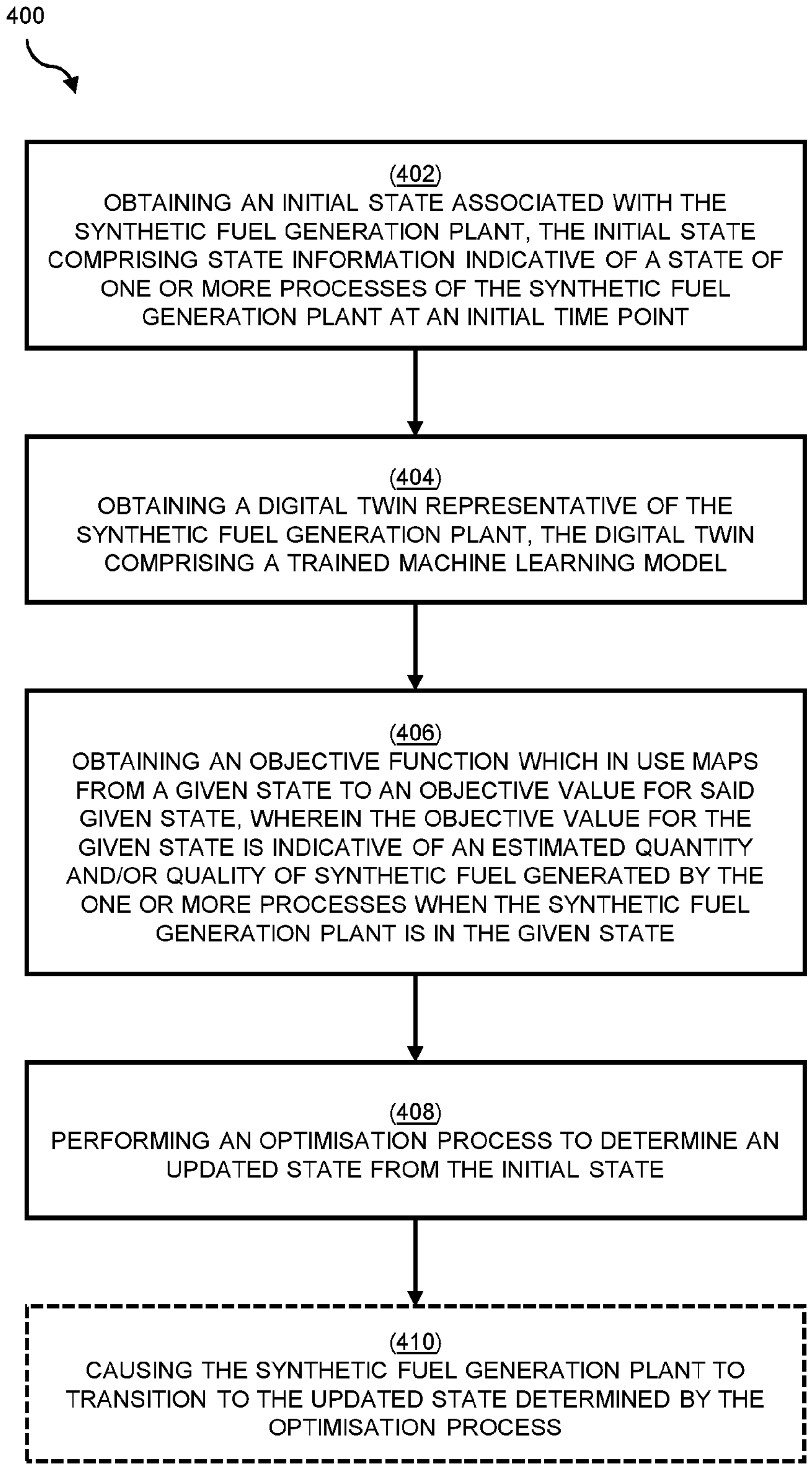
FIG. 4 shows a method for optimising a fuel generation process performed by a synthetic fuel generation plant according to an aspect of the present disclosure.

FIG. 4 shows method 400 for optimising a fuel generation process performed by a synthetic fuel generation plant.

Method 400 comprises steps 402, 404, 406, and 408. Method 400 optionally comprises step 410.

Step 402 comprises obtaining an initial state associated with the synthetic fuel generation plant, the initial state comprising state information indicative of a state of one or more processes of the synthetic fuel generation plant at an initial time point.

In an embodiment, the state information comprises a sensor value associated with a corresponding sensor of the synthetic fuel generation plant and the environment, wherein the sensor is associated with a process of the synthetic fuel generation plant.

Step 404 comprises obtaining a digital twin representative of the synthetic fuel generation plant. The digital twin comprising a trained machine learning model which in use: receives a first state associated with the synthetic fuel generation plant at a first time point; and predicts a first future state, wherein the first future state comprises predicted state information indicative of a future state of one or more processes of the synthetic fuel generation plant at a second time point subsequent the first time point.

In one embodiment, the trained machine learning model is a supervised machine learning model trained on a dataset of historical states. Preferably, the dataset of historical states is obtained from a plurality of fuel generation plants.

Step 406 comprises obtaining an objective function which in use maps from a given state to an objective value for said given state, wherein the objective value for the given state is indicative of an estimated quantity and/or quality of synthetic fuel generated by the one or more processes when the synthetic fuel generation plant is in the given state.

Step 408 comprises performing an optimisation process to determine an updated state from the initial state.

Figure 5:
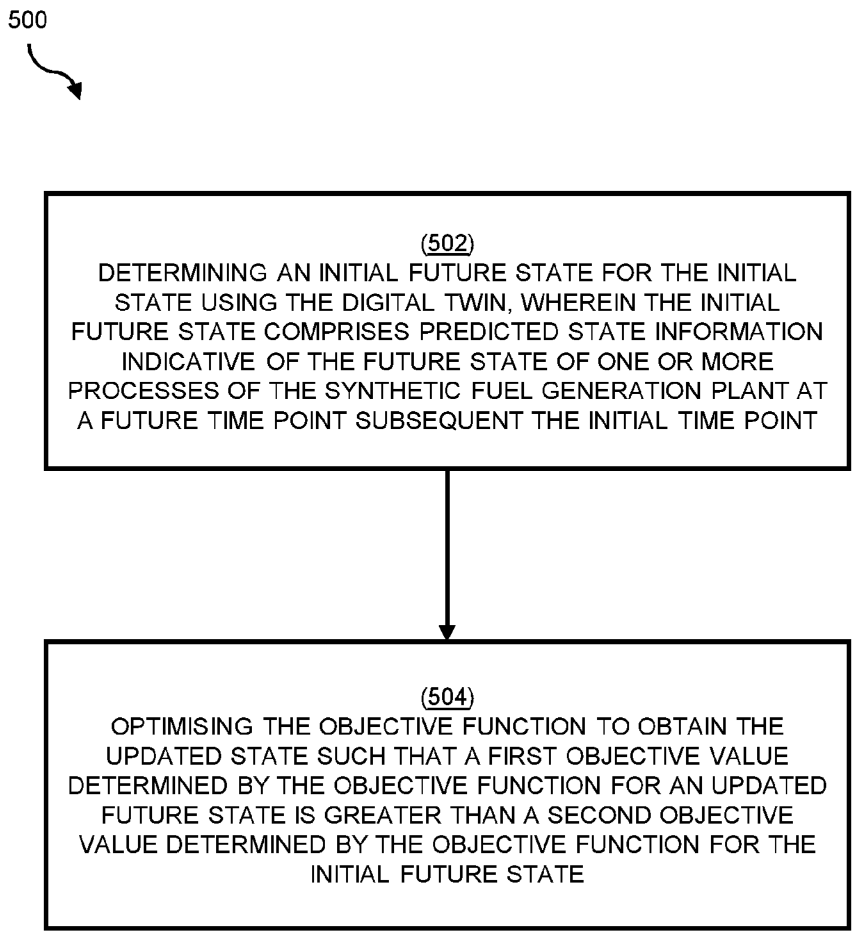
FIG. 5 shows an optimisation process according to an aspect of the present disclosure.

FIG. 5 shows optimisation process 500 according to an aspect of the present invention. Optimisation process 500 comprises steps 502 and 504.

Step 502 comprises determining an initial future state for the initial state using the digital twin, wherein the initial future state comprises predicted state information indicative of the future state of one or more processes of the synthetic fuel generation plant at a future time point subsequent the initial time point.

Step 504 comprises optimising the objective function to obtain the updated state such that a first objective value determined by the objective function for an updated future state is greater than a second objective value determined by the objective function for the initial future state. The updated future state is determined from the updated state by the digital twin, and the updated future state comprises predicted state information indicative of the future state of one or more processes of the synthetic fuel generation plant at the future time point.

In an embodiment, optimising the objective function is constrained by a predefined constraint, wherein the predefined constraint in use restricts the possible values of the state information of the updated state.

Returning once again to FIG. 4, method 400 optionally comprises step 410. Step 410 comprises causing the synthetic fuel generation plant to transition to the updated state determined by the optimisation process.

Optionally, method 400 further comprises determining an action plan to transition the synthetic fuel generation plant from the initial state to the updated state. Optionally, causing the synthetic fuel generation plant to transition to the updated state comprises causing an execution of the action plan by the synthetic fuel generation plant. Preferably, the action plan comprises a command to control an actuator of the synthetic fuel generation plant, wherein the actuator is associated with a processes of the synthetic fuel generation plant.

In one embodiment, method 400 further comprises causing a remote synthetic fuel generation plant to transition to the updated state determined by the optimisation process. Optionally, method 400 further comprises determining a remote action plan to transition the remote synthetic fuel generation plant to the updated state. Optionally, method 400 further comprises causing an execution of the action plan by the remote synthetic fuel generation plant.

Figure 6:
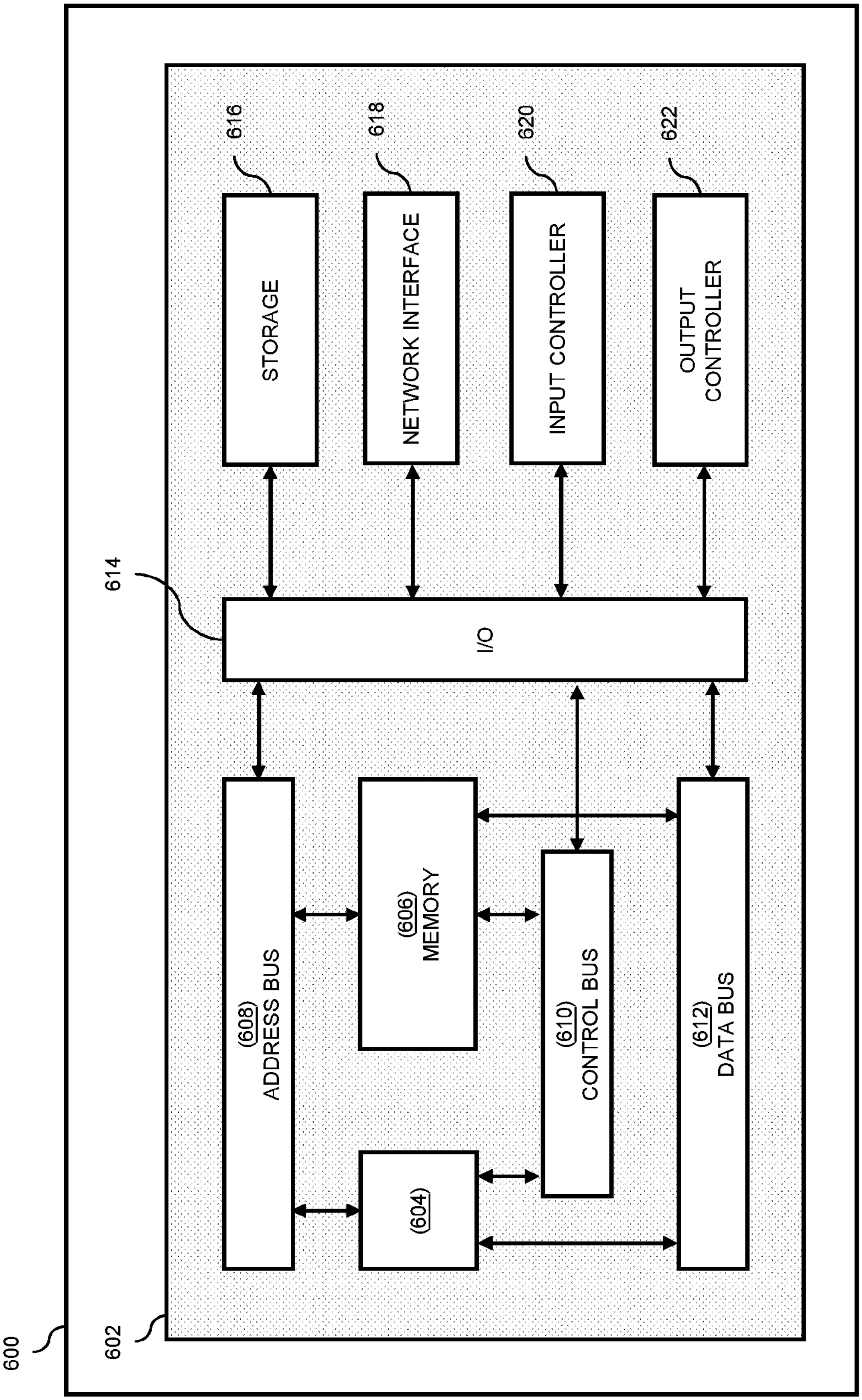
FIG. 6 shows an example computing environment.

FIG. 6 shows an example computing system. Specifically, FIG. 6 shows a block diagram of an embodiment of a computing system according to example embodiments of the present disclosure.

Computing system 600 can be configured to perform any of the operations disclosed herein such as, for example, any of the operations discussed with reference to control system 200 of FIG. 2. Computing system includes one or more computing device(s) 602. Computing device(s) 602 of computing system 600 comprise one or more processors 604 and memory 606. One or more processors 604 can be any general purpose processor(s) configured to execute a set of instructions. For example, one or more processors 604 can be one or more general-purpose processors, one or more field programmable gate array (FPGA), and/or one or more application specific integrated circuits (ASIC). In one embodiment, one or more processors 604 include one processor. Alternatively, one or more processors 604 include a plurality of processors that are operatively connected. One or more processors 604 are communicatively coupled to memory 606 via address bus 608, control bus 610, and data bus 612. Memory 606 can be a random access memory (RAM), a read-only memory (ROM), a persistent storage device such as a hard drive, an erasable programmable read-only memory (EPROM), and/or the like. Computing device(s) 602 further comprise I/O interface 614 communicatively coupled to address bus 608, control bus 610, and data bus 612.

Memory 606 can store information that can be accessed by one or more processors 604. For instance, memory 606 (e.g., one or more non-transitory computer-readable storage mediums, memory devices) can include computer-readable instructions (not shown) that can be executed by one or more processors 604. The computer-readable instructions can be software written in any suitable programming language or can be implemented in hardware. Additionally, or alternatively, the computer-readable instructions can be executed in logically and/or virtually separate threads on one or more processors 604. For example, memory 606 can store instructions (not shown) that when executed by one or more processors 604 cause one or more processors 604 to perform operations such as any of the operations and functions for which computing system 600 is configured, as described herein. In addition, or alternatively, memory 606 can store data (not shown) that can be obtained, received, accessed, written, manipulated, created, and/or stored. The data can include, for instance, the data and/or information described herein in relation to FIGS. 3 to 12. In some implementations, computing device(s) 602 can obtain from and/or store data in one or more memory device(s) that are remote from the computing system 600.

Computing system 600 further comprises storage unit 616, network interface 618, input controller 620, and output controller 622. Storage unit 616, network interface 618, input controller 620, and output controller 622 are communicatively coupled to central control unit or computing devices 602 via I/O interface 614.

Storage unit 616 is a computer readable medium, preferably a non-transitory computer readable medium, comprising one or more programs, the one or more programs comprising instructions which when executed by one or more processors 604 cause computing system 600 to perform the method steps of the present disclosure. Alternatively, storage unit 616 is a transitory computer readable medium. Storage unit 616 can be a persistent storage device such as a hard drive, a cloud storage device, or any other appropriate storage device.

Network interface 618 can be a Wi-Fi module, a network interface card, a Bluetooth module, and/or any other suitable wired or wireless communication device. In an embodiment, network interface 618 is configured to connect to a network such as a local area network (LAN), or a wide area network (WAN), the Internet, or an intranet.

FIG. 6 illustrates one example computer system 600 that can be used to implement the present disclosure. Other computing systems can be used as well. Computing tasks discussed herein as being performed at and/or by one or more functional unit(s) (e.g., as described in relation to FIG. 3) can instead be performed remote from the respective system, or vice versa. Such configurations can be implemented without deviating from the scope of the present disclosure. The use of computer-based systems allows for a great variety of possible configurations, combinations, and divisions of tasks and functionality between and among components. Computer-implemented operations can be performed on a single component or across multiple components. Computer-implemented tasks and/or operations can be performed sequentially or in parallel. Data and instructions can be stored in a single memory device or across multiple memory devices.

Figure 7:
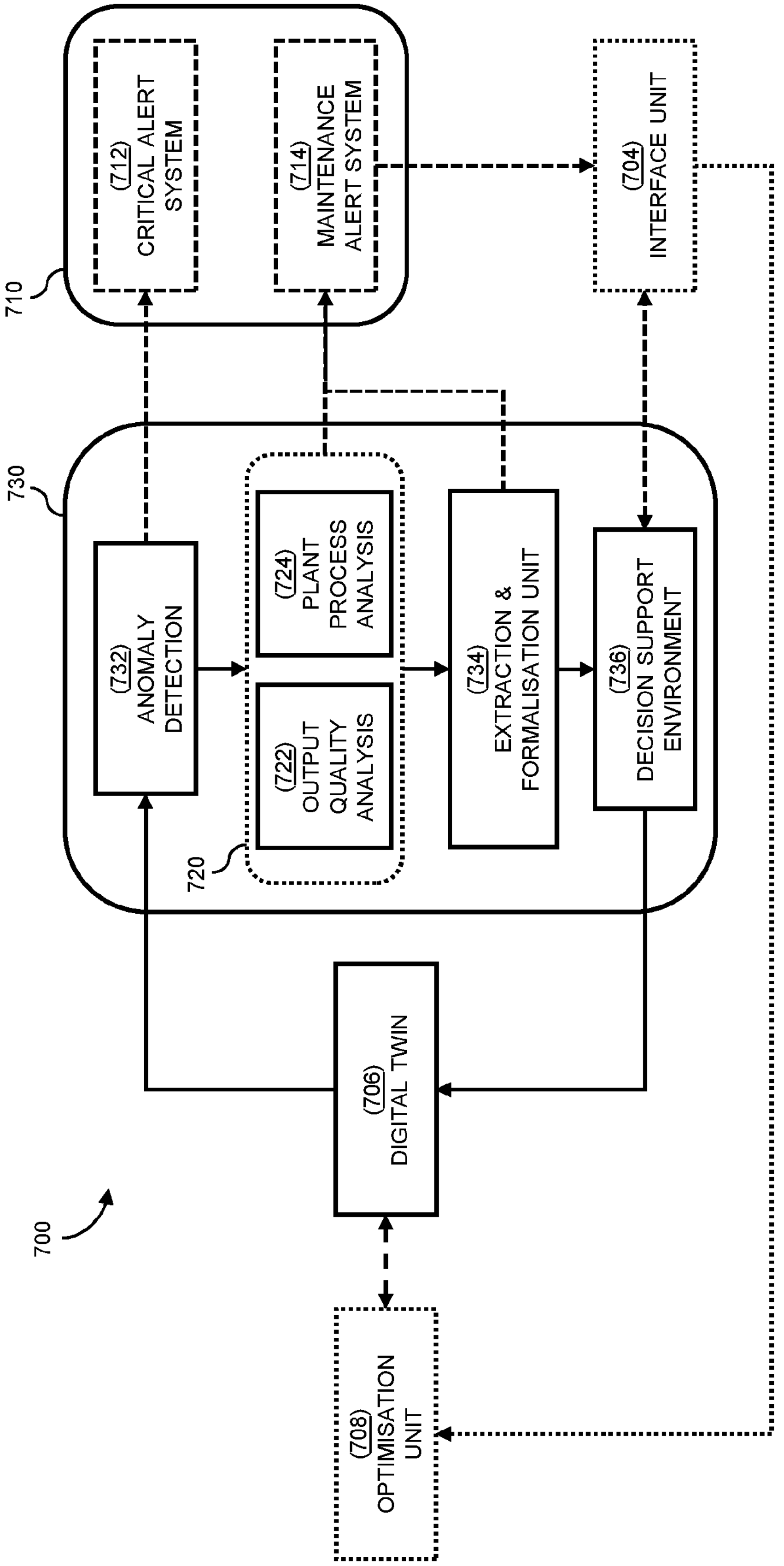
FIG. 7 shows an example reasoning support unit according to an aspect of the present disclosure.

FIG. 7 shows an example reasoning support unit according to one embodiment.

Reasoning support unit 700 interfaces with digital twin 706, which is an embodiment of the digital twin 206 of FIG. 2, interface unit 704, which corresponds to an embodiment of interface unit 204 of FIG. 2, and optimisation unit 708, which corresponds to an embodiment of optimisation unit 208 of FIG. 2. Reasoning support unit 700 comprises of validation unit 730, which corresponds to an embodiment of validation unit 230 of FIG. 2, and notification module 710. Validation unit 730 further comprises of anomaly detection module 732, analysis module 720, which further comprises output quality analysis 722 and plant process analysis 724, extraction & formalisation unit 734, and decision support environment 736. Notification module 710 comprises critical alert system 712 and maintenance alert system 714.

Information from digital twin 706 is processed by anomaly detection module 732, output to analysis module 720, further processed by extraction & formalisation unit 734, and then utilised by decision support environment 736. Decision support environment 736 feeds back into digital twin 706 and, optionally, communicates with interface unit 704. Both digital twin 706 and interface unit 704 may communicate with optimisation unit 708. In one embodiment, notification module 730 comprises of critical alert system 712, which receives information from anomaly detection module 732, and maintenance alert system 714, which receives information from analysis module 720 and extraction & formalisation unit 734.

Reasoning support unit 700 is configured to aid in qualitative and quantitative evaluation of updated states, through output quality analysis 722 and plant process analysis 724, provided by digital twin 706, for human, computational, or both human and computational interpretation, thereby increasing validation of the updated state. When a new state of the system is identified, or received, the reasoning support unit 700 provides an evaluation of the likely effect of the change, and furthermore provide human, and/or computational, under stable reasoning to aide a user of the system to understand the decisions made by the system as a result of the updated state. In the context of the synthetic fuel generation plant such reasoning allows an operator of the plant to determine, and understand, the likely effect of an updated system. Such information can support the decision making process, and provide information regarding an otherwise hidden, or internal state, of the system to the end user. Such information can be vital in the decision making process.

Within reasoning support unit 700, validation unit 730 is a functional unit that interfaces with digital twin 706, such that the digital twin 706 is dynamically adapted based on validation unit 730, which obtains data from digital twin 706. Digital twin 706, which is an embodiment of digital twin 206, is described in more detail in the description of FIG. 2. In one embodiment, reasoning support unit 700 comprises notification module 710, allowing for critical, current, or future alerts, such as maintenance alerts, to be generated as a result of information processed and evaluated within reasoning support unit 700.

Notification module 710 processes information of varying criticality from validation unit 730, and optionally communicates with interface unit 704. Critical alerts are generated from flagged anomalies in updated state data, and service and maintenance alerts are generated from additional analysis in updated state data, including predicted trends. Notification module 710 determines criticality and maintenance through comparison to pre-defined thresholds of criticality and maintenance or criticality and maintenance classifications. Optionally, critical and maintenance thresholds and classifications may be defined by anomaly detection module 732 or analysis module 720. Optionally, critical and maintenance thresholds and classifications may be defined by a human expert. Once a threshold criticality is reached or data is classified as critical, critical alerts are automatically distributed from critical alert system 712 to human operators, for manual intervention. In one embodiment, multiple optional scenarios are generated for the human operator, which can then be executed automatically by the system or manually be the human operator. Generation of action scenarios can be from selection of pre-defined actions or action generation can be performed by a suitable trained machine learning algorithm, such as a natural language processing (NLP) algorithm, for example a naïve Bayes algorithm. If a threshold or classification for maintenance is obtained, but not a threshold or classification for criticality, for example a single fluctuating sensor reading, a maintenance alert is automatically distributed from maintenance alert system 714 to interface unit 704 to communicate a potentially faulty sensor. Optionally, interface unit 704 processes the maintenance alert and communicates maintenance information to optimisation unit 208 or action unit 212. In one embodiment, critical alerts are automatically distributed to automated modules for automated actions, or to both automated modules and human operators. In one embodiment, maintenance alerts are automatically distributed to human operators for manual evaluation or plant servicing.

Validation unit 730, an embodiment of validation unit 230, interfaces with digital twin 706, and optionally interface unit 704. Validation unit 730 receives updated state information from digital twin 706 for further analysis and processing, which may include independent chemical and non-chemical analysis via output quality analysis 722 and plant process analysis 724, feature extraction, data formalisation, and other relevant processes to aid quantitative and qualitative synthetic fuel cell generation evaluation. Outputs may include interactive visualisations on status monitoring, trends in quality and quantity, and predictions. Additional outputs may include critical information such as mechanics requirements, and relevant historical information.

Anomaly detection module 732 processes information directly from digital twin 706 for automated anomaly detection. In an embodiment the anomaly detection module 732 is a suitable AI classification algorithm, such as an SVM, designed to flag differences and evaluate the criticality of these anomalies and trained with datasets of deviations between sequential updated states, or deviations between an updated state and the state of another plant, or deviations between an updated state and a previous state. As previously described for optional pre-processing of data, anomaly detection can be performed using any suitable known approach such as density-based techniques, cluster analysis, fuzzy logic-based outlier detection, and one-class support vector machines. Such an AI algorithm utilises supervised and/or semi-supervised machined learning. Example sources of an anomaly could be an error in hardware, such as a broken sensor, an error in data propagation resulting in an improbable or impossible sensor reading, or a large deviation in updated state provided by digital twin 706 compared to previous updated states. Such a deviation could be a fault in digital twin 706, a critical change in plant operation, or other situations related to the status of the plant. For example, output quality analysis 722 can determine that levels of crystalline catalysts required for the CDP process in combination with predicted pressure and temperature readings inside the plant are going to result in lower quality fuel compared to current production. This sudden drop in fuel quality is then detected by anomaly detection module 732. In an example when a deviation of a parameter is beyond an acceptable predetermined threshold it is flagged as a critical anomaly. In an embodiment a flagged critical anomaly generates an automated notification through direct communication with critical alert system 712 in notification module 710. A human operator can then be notified of the anomaly, evaluate the anomaly, and react accordingly. In one embodiment, evaluation of the anomaly is automated by anomaly detection module 732, which generates a ranked list of anomalies with criticality. Generation of a ranked list can be performed by a suitable trained machine learning algorithm, such as a natural language processing (NLP) algorithm, for example a naïve Bayes algorithm. Optionally, anomaly detection module 732 can detect several subgroups of anomalies.

The training and application of anomaly detection module 732 is detailed as a non-limiting example of an embodiment. The data for anomaly detection module 732 comprises data libraries of multiple layered data ontologies as described in FIG. 7 below, which may have been processed using methods of FIG. 7, FIG. 8, FIG. 9, or FIG. 10. The data may include manually produced data; synthetic data; data collected through manual processes; data collected through semi-automatic process; data collected through fully automatic processes; automated manually labelled data; unlabelled data; or automated or manually clustered data. In this example, the data includes both labelled and unlabelled data with statistical and contextual anomalies. Additional relevant data is added to the data libraries to generate a larger dataset for training through suitable data augmentation methods known in the field in combination with data mining methods described in FIG. 7. Augmentation methods can include back translation, AutoAugment, and TF-IDF word replacement. Management of data libraries is semi-automated, with automated data segmentation through suitable clustering algorithms and monitoring by human experts. The core machine learning module is a semi-supervised SVM algorithm, making use of both labelled and unlabelled data in the data libraries, and trained using any standard method known in the field including, for example back propagation, cascade training and parallel training. The trained model input is multimodal data including the current information from the plant (such as data from sensors over the last 10 minute window). The output is then the detection and risk associated with anomalies in the input. For example, input can include a temperature reading that is 50% higher than surrounding temperature readings, and the output is an anomaly with a medium risk. Risk can be quantitative, descriptive, or classifications. In this scenario, there are four risk categories: low, medium, high, and critical. For descriptive risk output, the core machine learning module is a semi-supervised NLP algorithm, such as PyramidNet+ ShakeDrop, trained using a combination of pre-training, self-training, and consistency training techniques known in the field, such as where consistency loss in minimised. This allows for labelled data to be used for correct predictions about unlabelled data during training. In application, this results in an easily understood ranked list of anomalies that can be used by both humans and automated modules.

Updated state information and anomaly information is processed by the analysis module 720. Chemical process specific information is analysed by output quality analysis 722, while plant process analysis 724 analyses information that is not chemical process specific. The chemical processes involved in a synthetic fuel generation plant are complex, so output quality analysis 722 is configured to analyse processes linked to quality parameters, such as maintaining the quality of fuel in the predefined range. Other quality parameters can include quantity of fuel, water, carbon dioxide, and sludge. Plant process analysis 724 is configured to analyse processes linked to, for example, quantity parameters or mechanical processes, such as determining potential output and energy consumption of the updated state. In one embodiment, analysis module 720 comprises one suitable algorithm capable of analysing both chemical and non-chemical specific processes. Optionally, analysis module 720 predicts current necessary maintenance and potential future maintenance for pro-active plant maintenance and optimisation. Preferably, analysis module 720 communicates directly with maintenance alert system 714 in notification module 710.

In one embodiment, analysis module 720 is a trained suitable machine learning algorithm, such as a multi-output linear regression model or a deep neural network, for example a U-Net or SVM with multiple input and output parameters capable of processing updated state information from digital twin 706, for example data on hydrocarbons, temperature, pressure, humidity, current and predicted supply, and energy consumption. Algorithms are trained following known training methods for the chosen algorithms on datasets containing relevant information, such as deviations between an ideal and observed state. Optionally, training data comprises synthetic modelled states or observed states from fully automated, semi-automated, or non-automated plants. Optionally, analysis module 720 and anomaly detection module 732 are a combined as a single or connected series of suitable trained machine learning algorithms as detailed above.

In one embodiment, analysis module 720 and anomaly detection module 732 are a series of models comprising a material flow patterns model, a model for lead times for a variety of input materials, an uncertainty model, a capacity statistical model, a machine availability and breakdown model, a human workforce uncertainty model, a technological process model, a deviation model between ideal model and observed realizations, a logistics demand forecasting model and a short-term model. These models comprise of both supervised methods, for example supervised neural networks such as a convolutional neural network, support vector machine, k-nearest neighbours, Bayesian networks and decision trees, as well as unsupervised methods such as K-means, GMMs, PCAs, for risk assessment and discrete event sequences. Models are chosen and trained based on standard methodologies in the field. For example, image classification from a camera sensor to identify input materials is performed by a convolutional neural network trained using standard neural network training methods with a dataset of pre-classified images of materials likely to be imaged by the camera sensor.

Extraction & formalisation unit 734 extracts information, rules, and concepts from analysis module 720. Extraction & formalisation unit 734 is a form of data contextualisation unit as it adds context to the plant state data. Extracted feature data is transformed into formalised descriptions in the form of if-then rules or semantic networks presented in resource description frameworks, or other models for encoding semantic relationships between items of data so that these relationships can be interpreted computationally or visually. Extraction & formalisation unit 734 uses data mining algorithms, such as stream mining and text mining, for knowledge extraction and association rules for knowledge formalisation. Optionally, formalised data is communicated to notification module 710 for proactive maintenance, and notification module 710 transfers data from extraction & formalisation unit 734 to a knowledge base of one or more plants.

In one embodiment, extraction & formalisation unit 734 adds extracted and formalised features to data libraries to be accessed by additional synthetic fuel generation plants, or used by the plant at a future time, such as after 1 month to 1 decade, for example after 6 months. Optionally, extraction & formalisation unit 734 generates a new data library. Data libraries may consist of multiple layered data ontologies and knowledge bases, for example: one data ontology focussed on capturing general plant processes, including input and outputs to the plant and mechanical specific dependencies, which can include pre-described actions for managing the process, such as starting the process, stopping the process, and cleaning relevant sensors and equipment for optimal operation of the process; another ontology based on sensor readings focussed on the specific chemical processes undertaken by the plant as previously described; and a pre-defined knowledge base of relevant chemical reactions and theory. In an example the knowledge base is created through data mining, such as web mining of publicly accessible internet pages, performed by algorithms such as clustering analysis, association rule learning models, or regression analysis models. Formalised data is stored using a suitable style for the collected data, such as resource descriptive framework (RDF) style. Optionally, digital twin 706 is trained using data comprising of a data library consisting of the two data ontologies disclosed above.

Decision support unit 736 transforms data from extraction & formalisation unit 734 into understandable visualisations for evaluation and validation of the updated state. These can include status monitoring, long-term and short-term trends, and predictions, as well as critical information such as the mechanics of the plant, relevant historical information, the process quality, and output quantities. Context, such as future incoming supplies to the plant, is supplied from interface unit 704 and integrated into decision support unit 736, so varied inputs do not disrupt the quality of fuel generated. Contextual integration is described in more detail below. Optionally, extraction & formalisation unit 734 and decision support unit 736 are a combined utilising a suitable multimodal machine learning algorithm, such as deep multimodal architectures including a Boltzmann machine, or a series of models, such as any previously described. In one embodiment, anomaly detection module 732, analysis module 720, extraction & formalisation unit 734 and decision support unit 736 are a combined suitable multimodal machine learning algorithm, which would include any previously described. Therefore, the decision support unit 736 allows an end user to understand the decisions made by the system, thus providing them with a level of insight into the decision which would otherwise remain hidden. Such information can help and inform the user when running a synthetic fuel plant.

Output from decision support unit 736 is in the form of graphical or textual output. The output preferably comprises: a title, such as "No input material"; a description, which for example would include a prediction of when input material will stop for the plant, details on how that will impact plant operation, as well as additional contextual information, for example when the next batch of input material is due and possible causes for the delay; a severity, corresponding to whether this is a critical incident, whether maintenance is required, whether it requires monitoring, or none of these; when the output was generated, for example a date and time, as well as how long ago that was; persons notified, including whether notification module 710 was activated; the current and predicted output of the plant, for example a percentage split between carbon dioxide, fuel, water, and other matter now and after the predicted updated state; and technical information, such as data for monitoring the operation of digital twin 706 and synthetic fuel generation plant 202. Optionally, text is generated using a suitable natural language processing (NLP) algorithm, such as a term frequency and inverse document frequency (TF-IDF) algorithm, naïve Bayes algorithm, or long short-term memory (LSTM) neural network architectures. The suitable NLP algorithms can be supervised, semi-supervised, or unsupervised, and training data can comprise of manually generated decision support information, synthetically generated decision support information based on manually generated samples, or data libraries of relevant information.

The output of decision support unit 736 is generated by the NLP which combines the results of the updated state information with the contextually relevant information for each state. As previously described, the data is enriched by data libraries at the extraction & formalisation unit 734 which utilises the existing data ontologies to provide enriched information such as formalised naming, definitions, relationships etc. This enriched data is combined with the updated state information to provide the output in a human understandable format.

Context is calculated by an automated process, allowing parts of the contextualised updated state information to be mapped to existing data ontologies within the data libraries. Structural and relational parts of the ontologies can be changed depending on the updated state information through human intervention for validation and confirmation. Optionally, digital twin 706 is contextualised directly for mapping to relevant data at a parameter level within the model, bypassing human confirmation for automated parameter changes. Casual, spatial, and temporal reasoning is extracted from the mapped, contextualised, updated state information through linked data from data libraries and formalised using any suitable style for linked collected data, such as an RDF graph. Optionally, decision support unit 736 displays the extracted reasoning without additional processing.

The training and application of decision support unit 736 is detailed as a non-limiting example. The data for training decision support unit 736 comprises data libraries of multiple layered data ontologies as previously described. These may include manually produced data; synthetic data; data collected through manual processes; data collected through semi-automatic process; data collected through fully automatic processes; automated, manual, or un-labelled data; or automated or manually clustered data. Examples within a data ontology for chemical processes include manually labelled and produced information from knowledge bases on chemical reactions, and information on chemical reactions collected and grouped using web mining techniques known in the field. Through previously described enrichment and contextualisation methods, additional relevant data may be added to the data libraries to generate a larger dataset for training. Augmentation methods can include back translation, AutoAugment, and TF-IDF word replacement. Management of data libraries is semi-automated, with automated data segmentation through suitable clustering algorithms and monitoring by human experts. The core machine learning module is a semi-supervised NLP algorithm, such as PyramidNet+ShakeDrop, making use of both labelled and unlabelled data in the data libraries, trained using a combination of pre-training, self-training, and consistency training techniques known in the field, such as where consistency loss in minimised. This allows for labelled data to be used for correct predictions about unlabelled data during training. The trained model is then input enriched and formalised data, which is multi-modal due to added contextualisation, and produces an output in the form of generated text and numerical data, as previously described. In application, this results in an easily understood reasoning of an analysed future state prediction that can be used by both humans and automated modules.

A predicted updated state is communicated from digital twin 706 to validation unit 730, where it is analysed and formalised for both automated and manual validation. This is then communicated back to digital twin 706, forming a continual loop of digital twin 706 validation, with the option of improvement. Information from digital twin 706 is input to anomaly detection module 732, which is optionally an embodiment of cleaning process 824 of FIG. 8 and is disclosed in detail below. If there are anomalies detected, information is communicated to notification module 710. If detected anomalies require alteration to plant operation, information is communicated to interface unit 704 and then to optimisation unit 708. Additionally, digital twin 706 communicates directly with optimisation unit 708. After anomaly detection module 732, information is analysed by analysis module 720, where output quality analysis 722 and plant process analysis 724 allow for plant process-specific analysis of the updated state. Extraction & formalisation unit 724 further processes the analysed information for important and relevant features, which is then formalised into a state usable by both machines and humans. Both analysis module 720 and extraction & formalisation unit 724 can communicate potential current and future maintenance requirements to notification module 710 for proactive and predictive plant maintenance. Information is then transformed into interactive visualisations by decision support environment 736, which can include status monitoring and critical information. These visualisations provide reasoning and context to updated state predictions for human, and automated, validation of digital twin 706. Decision support environment 736 communicates directly to both digital twin 706 and interface unit 704 allowing for alterations and improvements to both digital twin 706 and plant operations. An example embodiment of the reasoning support process illustrated in FIG. 7 is shown in FIG. 9 and detailed below.

Figure 8:
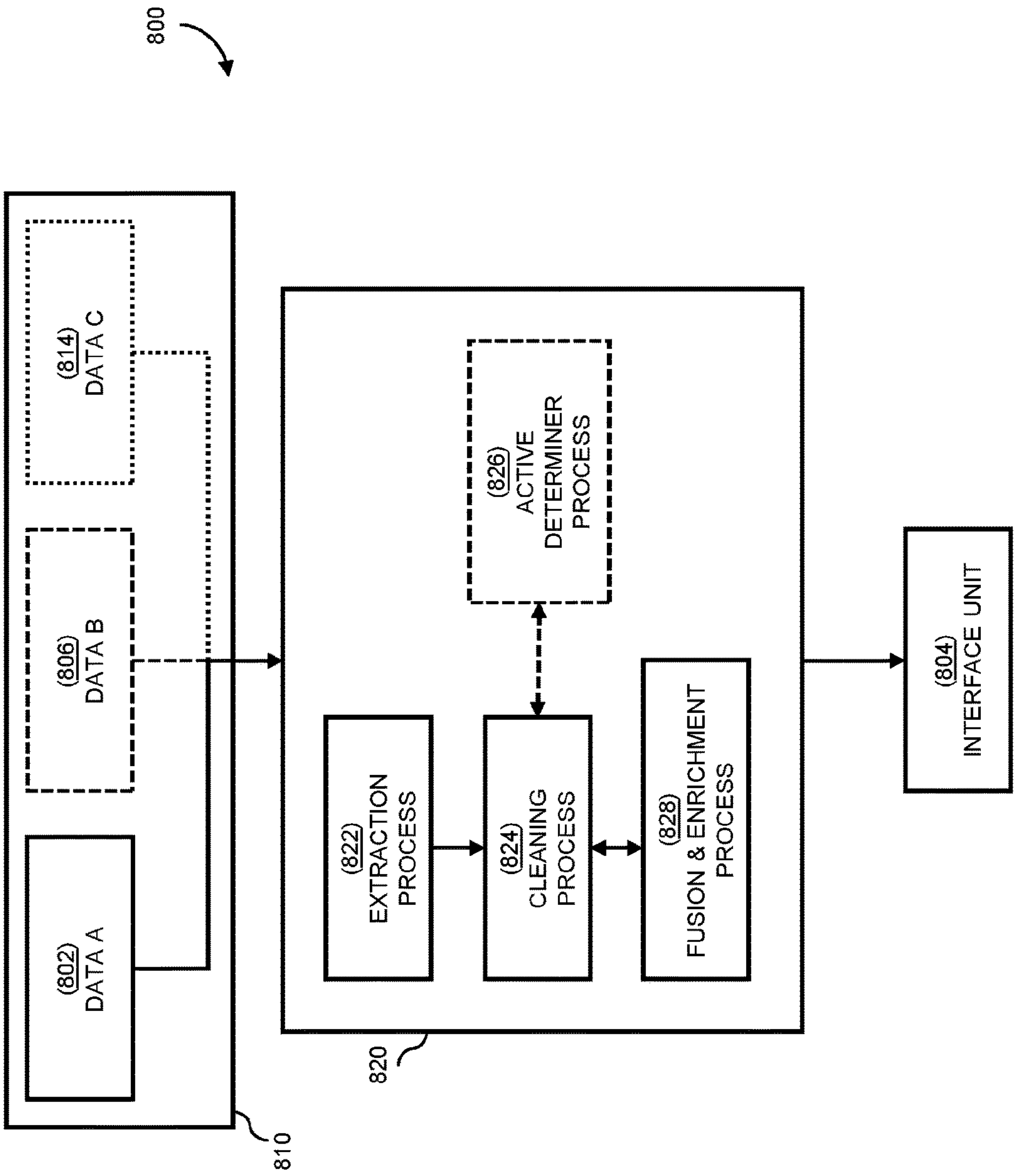
FIG. 8 illustrates an embodiment of a data fusion method according to an aspect of the present disclosure.
Figure 9:
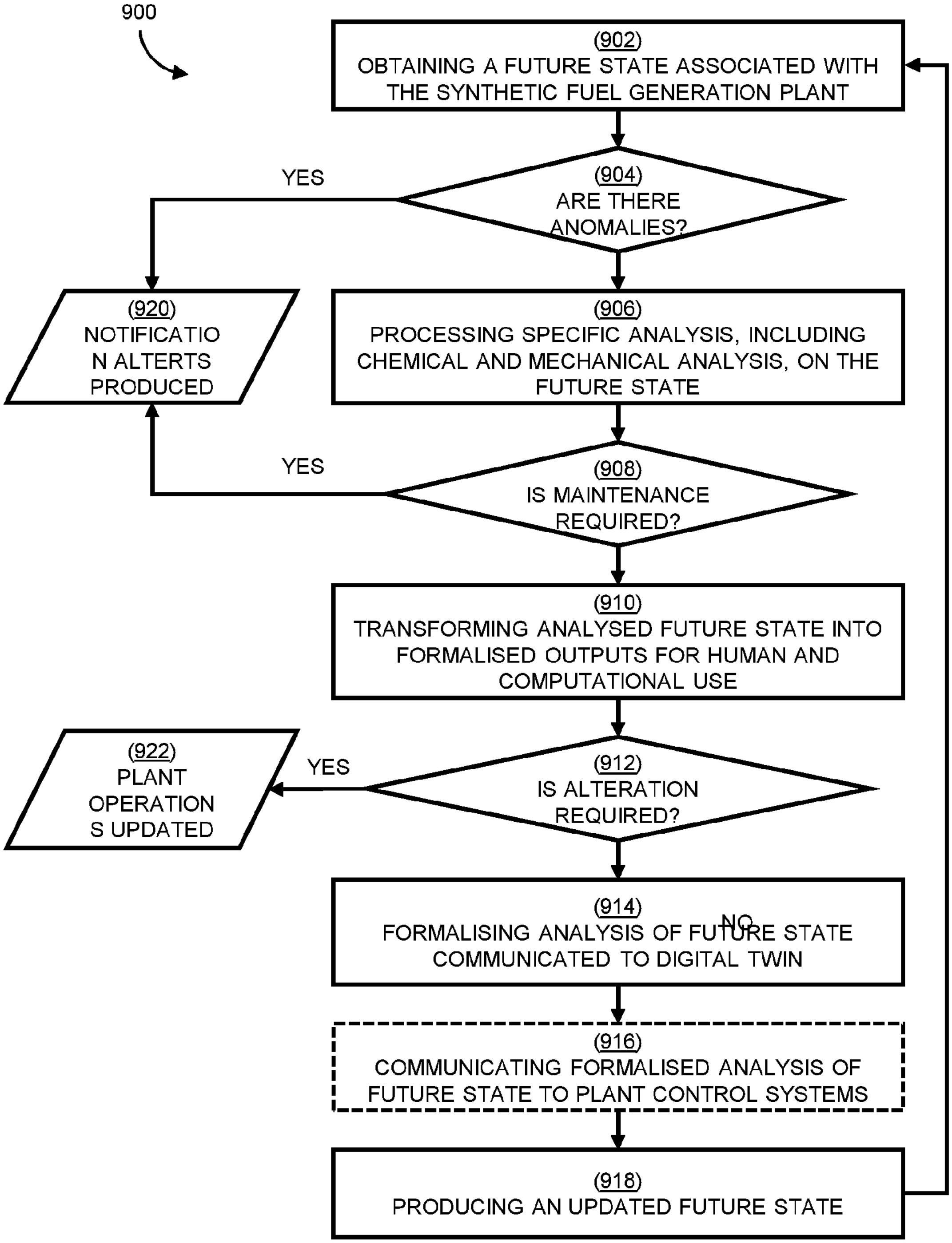
FIG. 9 shows a reasoning support process method according to an aspect of the present disclosure.

FIG. 8 illustrates an embodiment of a data fusion method according to an aspect of the present disclosure. Data fusion method 800 comprises data section 810, feeding into data transformation module 820, which transfers data to interface unit 804, which corresponds to an embodiment of interface unit 204 of FIG. 2 and interface unit 704 of FIG. 7. Data selection 810 comprises of data A 802, which corresponds to data from synthetic fuel generation plant 202 from FIG. 2, data B 806, and data C 814, which corresponds to data from remote fuel generation plant 214 from FIG. 2. Data transformation module 820, which corresponds to an embodiment of data transformation 220 in FIG. 2, comprises of extraction process 822, leading to cleaning process 824 and active determiner process 826, feeding on to fusion & enrichment process 828, which then communicates directly to interface unit 804.

Data fusion method 800 is a method for the combining, cleaning, and pre-processing multiple data types, such as text, images, and data streams, from multiple sources, such as sensors, cameras, and historical data from other plants.

Data selection 810 encompasses the data input to data transformation module 820, comprising of data A 802, data B 806 and data C 814. Data selection 810 is multi-modal, such as structured numerical data, unstructured textual data, image data, video data, and data streams. Data A 802 comprises of sensor readings from a local plant, corresponding to an embodiment of data from synthetic fuel generation plant 202 from FIG. 2. Data B 806 comprises of optional data that includes information on external factors relevant to plant operation, such as natural environmental data, for example weather forecasts both locally and for areas that impact imports and exports from the plant. Additional examples include external temperature, humidity, pressure, dust particles, supply chain data, supplier historical data, waste market information, and fuel market information, which are all relevant for optimal plant operation. Optimal outcomes can be calculated by a range of methods, including mathematical optimisation methods such as Difference Approximations, Discretization Methods, Gradient Projection Methods, Homotropy Methods, KKT Reduction Methods, Nonlinear Simplex Methods, complex constraint logic programming methods and forward chain reasoning, and is previously described in more detail.

Data transformation module 820 comprises of several data processes including extraction process 822, cleaning process 824, and fusion & enrichment process 828. Optionally, data transformation module 820 comprises of active determiner process 826. Each is a data processing module that together form a data processing system to transform multiple data types from multiple sources into a format suitable for machine and human interpretation and is used by the synthetic fuel generation plant described. Optionally, data transformation module 820 is a series of trained machine learning algorithms, such as suitable models previously disclosed, or a single trained machine learning algorithm suitable of processing and transforming multi-modal data, such as a supervised multi-modal deep neural network.

Extraction process 822 extracts important information from data selection 810 using standard feature extraction methods, such as name entity extraction, co-reference, relation extraction, and scale-invariant feature transform (SIFT) features. Extracted information from data A 802, data B 806, and data C 814 is presented in a common description in preparation for cleaning process 824.

Cleaning process 824 detects anomalies is data from extraction process 822 through finding irregularities. Statistical irregularities are detected using standard statistical analysis methods. Contextual irregularities are detected using a range of methods, including comparisons between data selection 810 at different time points and between different data sources, such as between data A 802 and data C 814. For example, a faulty sensor would provide a faulty sensor reading, which is detected by cleaning process 824 by comparing previous sensor readings in the same plant or comparing sensor readings of different plants. Additional methods include thresholding, automated classification through methods previously described such as data clustering, manual pre-classification, and other suitable methods. Cleaning process 824 determines whether data is relevant, such as whether extracted information from data B 806 is necessary for plant function. Optionally, cleaning process 824 analyses irregularities for critical or maintenance events, as described previously, for communication with notification module 710 of FIG. 7, either directly or through communication with interface unit 804, which is an embodiment of interface unit 704 of FIG. 7. Optionally, cleaning process 824 communicates with fusion & enrichment process 828 for additional contextual information.

Optionally, automated analysis is performed using any suitable algorithms previously disclosed, for example an SVM trained on historical states. For example, each irregularity is assigned a confidence level, corresponding to the certainty behind the source of the irregularity, and certainty behind whether there is an irregularity present. There are at least two confidence levels, where a first confidence level corresponds to low confidence, when the presence or source of an irregularity is unclear, and a second confidence level corresponds to high confidence, when the presence or source of an irregularity is clear. Irregularities in the first confidence level are transferred to active determiner process 826.

Active determiner process 826 assists cleaning process 824. Any irregularity that requires additional analysis, such as an irregularity with an unknown source, or data that may or may not be an irregularity, is transferred from cleaning process 824 to active determiner process 826. In one embodiment, active determiner process 826 is a semi-automated process utilising an algorithm capable of interfacing human interaction, such as an active learning algorithm. As previously described for optional pre-processing of data, active learning is a subset of machine learning whereby a machine learning algorithm can query a human in order to provide further information regarding state values. In one embodiment, this process is automated through suitable trained machine learning algorithms, for example a support vector machine (SVM), or other algorithms based on data clustering methods, such as K-Means clustering, trained using methods known in the field. Optionally, this process is automated through use of suitable software modules, such as X-Pack and Coralogix in Java. Optionally, active determiner process 826 is a human operative. Active determiner process 826 determines whether there is an irregularity and the source of that irregularity and transfers this information to cleaning process 824. Optionally, cleaning process 824 is adjusted with each interaction with active determiner process 826 such that cleaning process 824 improves determination of irregularities and the corresponding sources.

Fusion & enrichment process 828 integrates all data such that multiple types of data from multiple sources are fused such that cleaned data A 802 is enriched with data from external and contextual sources, such as cleaned data B 806 and data C 814. Data is fused using time windows, where each time window is optionally between 1 minute and 1 hour and is preferably 10 minutes. Fusion & enrichment process 828 is a form of data contextualisation unit as it adds context to the plant state data. Each data type collected within or referencing a time within the selected time window is grouped together using an automated process. Contextual sources include sensor readings, such as data A 802 and previous states of one or more additional plants, such as data C 814, and can optionally contain any suitable pre-collected and real-time data in which relevant data can be extracted, such as data B 806. A contextual matching algorithm, for example a semi-supervised knowledge graph generation model, groups relevant information through a mixture of defined and automated information classification. Optionally, contextual matching can be entirely automated. A contextual matching graph produced from fusion & enrichment process 828 is formatted for both machine and human use. Contextual matching, using predefined knowledge, adds reasoning and relevant factors for digital twin 206 from FIG. 2, generating smoother operations. For example, contextual data on future incoming supply leads to modification of automated plant operation, resulting in the same quality output when input materials are changed. In one embodiment, the contextual matching graph is produced using a suitable style for linked collected data, such as an RDF graph, using methodology described above for an embodiment of decision support environment 736 of FIG. 7.

The training and application of fusion & enrichment process 828 is detailed as a non-limiting example. The data for fusion & enrichment process 828 comprises data libraries of multiple layered data ontologies as previously described. These may include manually produced data; synthetic data; data collected through manual processes; data collected through semi-automatic process; data collected through fully automatic processes; automated, manual, or un-labelled data; or automated or manually clustered data. Examples within a data ontology for material inputs and outputs include manually labelled images from knowledge bases on likely input materials, and information on potential carbohydrate sources collected and grouped using web mining techniques known in the field. Additional relevant data is added to the data libraries to generate a larger dataset for training through suitable data augmentation methods known in the field in combination with data mining methods previously described. Augmentation methods can include back translation, AutoAugment, and TF-IDF word replacement. Management of data libraries is semi-automated, with automated data segmentation through suitable clustering algorithms and monitoring by human experts. The core machine learning module is a semi-supervised NLP algorithm, such as PyramidNet+ShakeDrop, making use of both labelled and unlabelled data in the data libraries, trained using a combination of pre-training, self-training, and consistency training techniques known in the field, such as where consistency loss in minimised. This allows for labelled data to be used for correct predictions about unlabelled data during training. The trained model is then input data A 802, data B 806, and data C 814, including potentially relevant contextual information, which is multi-modal due to multiple data types and sources, and produces an output in the form of an RDF graph, as previously described. In application, this results in an easily understood mapping of contextual features to data A 802 that can be used by both humans and automated modules.

There is a variety of data input to the plant from data selection 810, which can include data A 802, information on the plant through, for example, sensor readings, data B 806, information on external factors such as temperature and humidity, and data C 814, information from one or more remote plants, and any historical data from synthetic fuel generation plant 202 of FIG. 2 or remote fuel generation plant 214 of FIG. 2. This information is processed by data transformation module 820 for input to interface unit 804. Data gathered can be in a form of different modalities, so extraction process 822 may use a multitude of methods to extract important and relevant features. After extraction process 822, information is cleaned by cleaning process 824, where anomalies and irregularities are detected and analysed, and queries are resolved by active determiner process 826. Information is then communicated to fusion & enrichment process 828, which fuses the data and enriches through added contextualisation from knowledge bases. Contextualised information can then return to cleaning process 824 for further analysis, communicated to interface unit 804 for use by the plant, or both. Through interface unit 804, an embodiment of interface unit 704 of FIG. 7, contextualised information is supplied to the operation of the plant (optimisation unit 708), updated state of the plant (digital twin 706), and reasoning and validation behind current and predicted plant operations (reasoning support unit 700).

Figure 10:
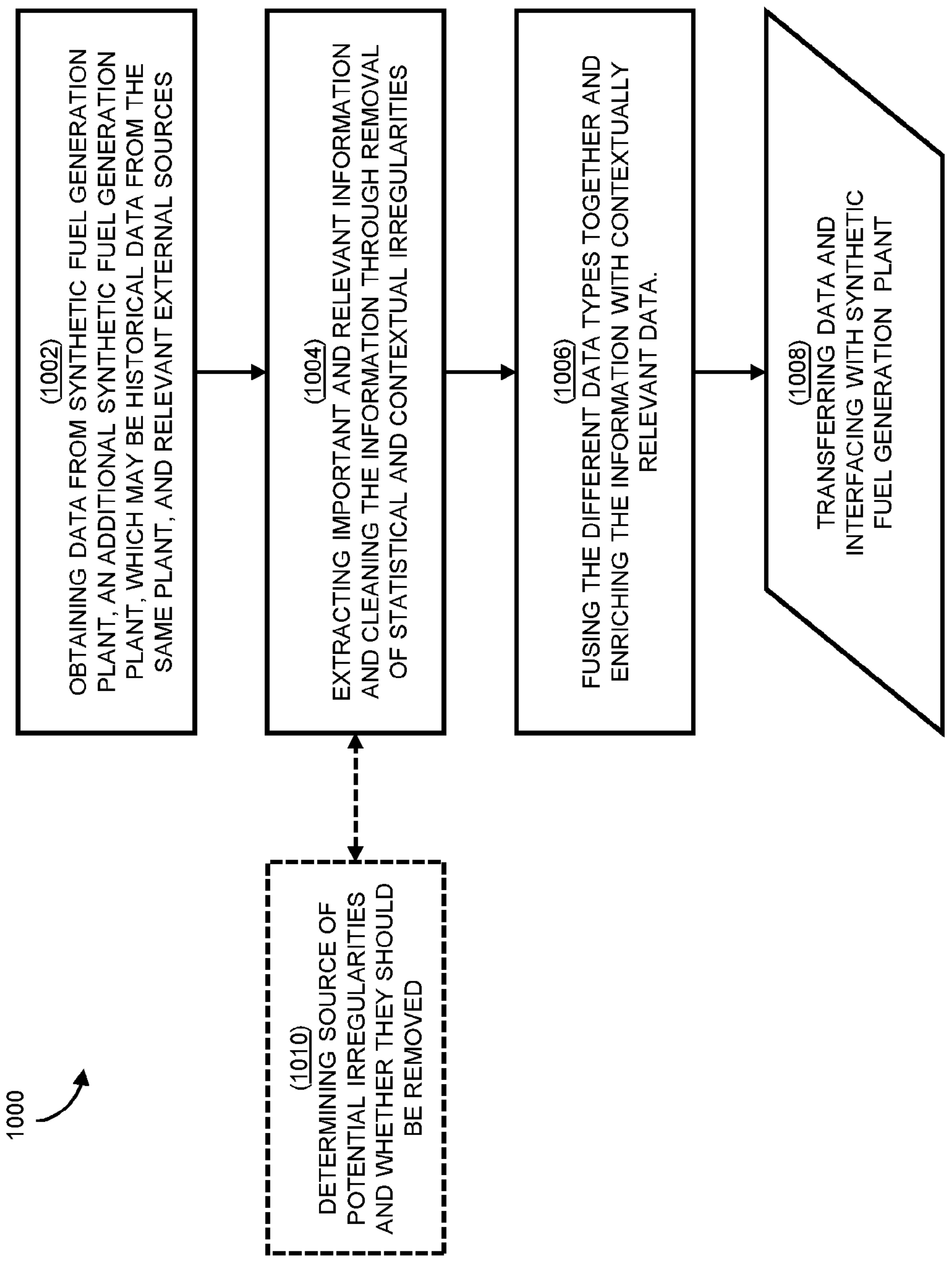
FIG. 10 shows a data cleaning and enrichment process according to an aspect of the present disclosure.

An example embodiment of the data cleaning and enrichment process illustrated in FIG. 8 is shown in FIG. 10 and detailed below.

FIG. 9 shows a reasoning support process method according to an aspect of the present disclosure.

Method 900 comprises steps 902, 904, 906, 908, 910, 912, 914, 918, 920, and 922. Method 900 optionally comprises step 916. In one embodiment, method 900 is a process undertaken by embodiments of validation unit 230, digital twin 206, interface unit 204, and optimisation unit 208 of FIG. 2.

Step 902 comprises obtaining a future state associated with the synthetic fuel generation plant. The future state is associated with synthetic fuel generation plant 202 of FIG. 2 and is generated by an embodiment of digital twin 206 of FIG. 2.

Step 904 comprises determining whether there are anomalies in the obtained future state from step 902. Example anomalies include statistical anomalies and contextual irregularities, such as resulting from a sensor malfunction. Anomaly detection is described in detail in FIG. 7 corresponding to anomaly detection module 732, and in FIG. 8 corresponding to cleaning process 824. In one embodiment, a detected anomaly is indicative of a critical event at an estimated future time point, such as a dangerous increase in temperature within 3 hours. Preferably the anomaly detection is performed by a suitable active learning machine learning algorithm, as previously disclosed. If anomalies are detected the process proceeds to step 920 to generate an alert. If no anomalies are detected the process proceeds to step 906.

Step 906 comprises process specific analysis, such as chemical analysis and mechanical analysis, on the obtained future state. In one embodiment, chemical analysis and non-chemical analysis are performed by separate suitable machine learning algorithms, such as neural networks, trained on process specific training data using straining methods known in the field, as previously disclosed. Determining whether a process is chemical or non-chemical is an automated through use of pre-defined knowledge bases within data libraries previously described in detail in the description of FIG. 7. As the data is enriched with the formalisation and ontology identification of the nature of the process being chemical or non-chemical can be made.

Step 908 comprises determining whether maintenance is required as a result of analysis on the future state. The determination of whether maintenance is required is as described previously. If maintenance is not required, the process proceeds to step 910. If maintenance is required, an alert is generated at step 920.

Step 920 comprises receiving anomalies and maintenance details and producing notifications to communicate alerts to both human and automated operators of the plant. In one embodiment, if the event is deemed to be critical, a critical event alert is communicated to interface unit 204. Dependant on the severity, for example determined by predetermined threshold, this results in an automated safe shut-down of the plant. In one embodiment, a maintenance alert is communicated to a human operator, resulting in the replacement of the malfunctioning sensor.

Step 910 comprises transforming the analysed future state into formalised outputs for use by both humans and automated operators. Therefore, at step 910 the output is transformed into a form understandable by the end user to allow them to understand, and have confidence, in the decisions made. As described above the formalised outputs may include relevant contextual information. Contextualisation and enrichment of data is described in detail in FIG. 7 corresponding to validation unit 730. As described above the use of the knowledge bases allows for the data ontology to be constructed, thus enriching the data with context specific information. This context specific information allows for the transformation of the future state into a formalised output. In one embodiment, the formalised outputs are a combination of generated text, interactive visualisations, and graphs to display information on the status of plant from the analysed future state. Optionally, human operators can use the formalised outputs to validate the future state predicted by digital twin 206. Optionally, digital twin 206 can use the formalised outputs to alter updated state predictions.

Step 912 comprises determining whether alteration of plant operation is required. In one embodiment, formalised outputs show the plant will require a change in synthetic fuel generation due to upcoming changes to input materials, such as upcoming supply chain issues, to maintain optimal operation. In one embodiment, optimal operation includes a pre-defined ratio of outputs such as fuel and carbon dioxide, and step 912 is an automated process, such as computational comparisons of predicted output ratios and desired output ratios reaching a threshold deviation. Optionally, step 912 can be performed by a human operator. If alteration of the state is required the process proceeds to step 922, if no alteration is required the process proceeds to step 914.

Step 922 comprises updating plant operation to maintain optimal operation, where alteration of plant operation is required as determined in step 912. In one embodiment, changes required are communicated to digital twin 206, which subsequently communicated with optimisation unit 208. Optionally, changes required are communicated to interface unit 204, which subsequently communicates with optimisation unit 208. Optionally, optimal operation for the plant is determined by optimisation unit 208.

Step 914 comprises communicating formalised analysis of the future state, where alteration of plant operation is not required as determined in step 912, to digital twin 206. As described above the digital twin 206 utilises the updated information in the optimisation process.

Step 916 comprises optionally communicating formalised analysis of the future state to plant control systems. In one embodiment, information is transferred to interface unit 204 for output to the end user as described above.

Step 918 comprises producing a new updated state. In one embodiment, digital twin 206 produces a new updated state based on both the analysed future state and new input data from the sources used to predict the future state. Preferably, this new updated state then becomes the future state of step 902, creating a continuous system.

An example of method 900 for a temperature sensor starts with step 902, is described below as a non-limiting example. The temperature sensor obtains a future temperature of 50° C. for a specific temperature sensor from digital twin 206. Step 904, the temperature is 5° C. higher than the average temperature obtained from multiple surrounding sensors, so is a detected irregularity. Step 908, due to the 5° C. deviation from surrounding sensors, the temperature sensor is determined to be potentially faulty, and maintenance is required. Step 920, 50° C. is within a pre-defined safe range, and therefore no critical alert is generated. Step 910, the temperature reading is analysed with the aid of contextually relevant data. In this example, historical readings show that the temperature sensor has been 5° C. higher than the average temperature for the last 2 hours, and that there is not a similar temperature gradient in a different plant. Step 920, a human operator is notified of a maintenance alert, suggesting an inspection of the temperature sensor. Step 912, as the sensor is possibly faulty, it is determined that the operation of the plant is not required to change based on the reading 50° C. Step 922, it is communicated to interface unit 204 that the specific sensor needs inspection, but no change is required. Step 914, it is communicated to digital twin 206 that the sensor is potentially faulty, and therefore digital twin excludes the readings from being used to model the next updated state. Step 916, communication to interface unit 204 leads to the exclusion of readings from this sensor being used in monitoring the conditions of the plant. Step 918, the digital twin produces a new updated state.

FIG. 10 shows a data cleaning and enrichment process according to an aspect of the present disclosure.

Method 1000 comprises steps 1002, 1004, 1006, and 1008. Method 1000 optionally comprises step 1010.

Step 1002 comprises obtaining data from synthetic fuel generation plant, an additional synthetic fuel generation plant, and relevant external sources. In one embodiment, data from synthetic fuel generation plant is data of multiple types, such as images and numerical data, obtained from multiple sensors throughout the plant. Optionally, data from an additional synthetic fuel generation plant is sensor readings from the same plant at a historical time point, such as 6 months ago. Data from relevant external sources may include external temperature, humidity, and supply chain information.

Step 1004 comprises extracting important and relevant information from obtained data, and cleaning this information by removing anomalies, including statistical anomalies and contextual irregularities. In one embodiment, data extraction is performed by a suitable feature extraction machine learning algorithm, such as a CNN for image data trained on labelled images of input materials, and data cleaning is performed by a suitable active learning machine learning algorithm, as previously disclosed. If anomalies are detected the process proceeds to step 1010. If no anomalies are detected the process proceeds to step 1006.

Step 1010 comprises determining the source of potential irregularities and whether the irregularities should be removed from the data. In one embodiment, an irregularity generated from an incorrect data entry, such as a typo from a human operator, is contextually different from historic data entries, but not different enough to be a clear statistical anomaly. This is determined to be an anomaly by a human operator and is removed from the data. Optionally, this process is automated through suitable trained machine learning algorithms, for example algorithms based on data clustering methods, such as K-Means clustering, trained using methods known in the field.

Step 1006 comprises fusing the different data types and sources together and enriching the information with contextually relevant data. This process is described in more detail in FIG. 7, corresponding to validation unit 730. In one embodiment, the data of different types and from difference sources are grouped using ontologies created through manual or automated classification, and through use of time windows. Data relevant to a specific time point within a defined time window between 1 second and 24 hours, such as 10 minutes, are also grouped together. Grouped data is then enriched using contextually relevant information, which can be sourced from pre-defined data libraries, such as background knowledge, or collected from varied sources such as social networks and media news feeds using suitable trained machine learning algorithms, such as regression or decision tree models, as previously described.

Step 1008 comprises transferring fused and enriched data to, and interfacing with, synthetic fuel generation plant. In one embodiment, fused and enriched data is communicated to an embodiment of interface unit 204 of FIG. 2.

A nonlimiting example of the method is provided for context. An example of method 1000 for data from a camera within the plant starts with step 1002, obtaining an image of input material from the synthetic fuel plant, an image of input material from the synthetic fuel plant 3 hours ago and accompanying plant information, and information on future supply to the plant. Step 1004, the materials and corresponding quantities are extracted from the image of input materials. However, part of the image data not recognised as a classified input material. Step 1010, the irregular section of the image is determined to be due to a build-up of dirt on the camera lens, and that section of data is discarded. Step 1006, data extracted from images from the last 10 minutes are combined to produce and average input of materials and quantity over the 10 minute time window. This is combined with a 10 minute time window of the plant 3 hours ago and the contextually relevant information from the plant in the same time window, such as the corresponding chemical process monitoring, and the output quality. This is also combined with contextually relevant information on future supply, such as whether the next input material is from the same source as the input now and 3 hours previously. The new combined and contextualised data is the current input to the plant, the comparative past input and the resulting corresponding output from 3 hours ago, and a decrease in input quantity is expected in the next supply. Step 1008, this data is transferred to interface unit 204, which can then be used by the plant and digital twin to stabilise output based not only on the current input materials, but also on the upcoming changes to the input.

In the present disclosure, references to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. The use of any and all examples, or exemplary language ("e.g.," "such as," "including," or the like) provided herein, is intended merely to better illuminate the embodiments and does not pose a limitation on the scope of the embodiments or the claims.

Some embodiments described herein may relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a transitory computer program product, which can include, for example, the instructions and/or computer code discussed herein.

Some embodiments and/or methods described herein can be performed by software (executed on hardware), hardware, or a combination thereof. Hardware modules include, for example, a general-purpose processor, a field programmable gate array (FPGA), and/or an application specific integrated circuit (ASIC). Software modules (executed on hardware) can be expressed in a variety of software languages (e.g., computer code), including C, C++, Java, Ruby, Visual Basic, Python, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The invention claimed is:

1. A control system for optimising a fuel generation process performed by a synthetic fuel generation plant, the control system comprising:

an interface unit configured to be communicably coupled to the synthetic fuel generation plant, the interface unit operable to:

obtain an initial state associated with the synthetic fuel generation plant, the initial state comprising state information indicative of a state of one or more processes of the synthetic fuel generation plant at an initial time point;

a data contextualisation unit configured to obtain contextual information regarding the initial state from a knowledge base and augment the data regarding the initial state with the contextual information;

a digital twin representative of the synthetic fuel generation plant, the digital twin comprising a trained machine learning model configured to:

receive a first state associated with the synthetic fuel generation plant at a first time point and the associated contextual information; and predict a first future state, wherein the first future state comprises predicted state information indicative of a future state of one or more processes of the synthetic fuel generation plant at a second time point subsequent the first time point; an optimisation unit in communication with the interface unit and the digital twin, wherein the optimisation unit is configured to:

obtain an objective function which in use maps from a given state to an objective value for said given state, wherein the objective value for the given state is indicative of an estimated quantity and/or quality of synthetic fuel generated by the one or more processes when the synthetic fuel generation plant is in the given state; and perform an optimisation process to determine an updated state from the initial state, the optimisation process operable to:

determine an initial future state for the initial state using the digital twin, wherein the initial future state comprises predicted state information indicative of the future state of one or more processes of the synthetic fuel generation plant at a future time point subsequent the initial time point; and optimise the objective function to obtain the updated state such that a first objective value determined by the objective function for an updated future state is greater than a second objective value determined by the objective function for the initial future state;

wherein the updated future state is determined from the updated state by the digital twin, and the updated future state comprises predicted state information indicative of the future state of one or more processes of the synthetic fuel generation plant at the future time point; and a reasoning support unit configured to provide an evaluation of the updated future state based on the updated future state information and the contextual information.

2. The control system of claim 1 further comprising:

an action unit configured to:

cause the synthetic fuel generation plant to transition to the updated state determined by the optimisation process.

3. The control system of claim 2 wherein the action unit is further configured to:

determine an action plan to transition the synthetic fuel generation plant from the initial state to the updated state.

4. The control system of claim 3 wherein, in order to cause the synthetic fuel generation plant to transition to the updated state, the interface unit is further configured to:

provide the action plan to the synthetic fuel generation plant for execution by the synthetic fuel generation plant.

5. The control system of claim 3 wherein the action plan comprises a command to control an actuator of the synthetic fuel generation plant, wherein the actuator is associated with a processes of the synthetic fuel generation plant.

6. The control system of claim 1 wherein the state information comprises a sensor value associated with a sensor of the synthetic fuel generation plant, wherein the sensor is associated with a process of the synthetic fuel generation plant.

7. The control system of claim 1 wherein the trained machine learning model is a supervised machine learning model trained on a dataset of historical states, wherein the dataset of historical states is obtained from a plurality of fuel generation plants.

8. The control system of claim 1, wherein the action unit is further configured to:

cause a remote synthetic fuel generation plant to transition to the updated state determined by the optimisation process.

9. The control system of claim 8 wherein the action unit is further configured to:

determine a remote action plan to transition the remote synthetic fuel generation plant to the updated state.

10. The control system of claim 9 wherein:

the interface unit is further configured to be communicably coupled to the remote synthetic fuel generation plant; and in order to cause the remote synthetic fuel generation plant to transition to the updated state the interface unit is further configured to:

provide the remote action plan to the remote synthetic fuel generation plant for execution by the remote synthetic fuel generation plant.

11. The control system of claim 1 wherein optimisation of the objective function is constrained by a predefined constraint.

12. The control system of claim 11 wherein the predefined constraint in use restricts possible values of the state information of the updated state.

13. The control system of claim 1 wherein the reasoning support system further comprises a natural language processor configured to provide a natural language output based on the updated future state information and the contextual information.

14. The control system of claim 1 wherein the data contextualisation unit is further configured to define an ontology for the initial state defined from said knowledge base and supplements the initial state with the ontology.

15. The control system of claim 14 wherein the data contextualisation unit is further configured to update state information to the ontology.

16. The control system of claim 1 wherein the system further comprises a data transformation unit configured to remove anomalies from data, and wherein the data transformation unit is configured to remove anomalies from the data by statistical analysis.

17. The control system of claim 16 wherein the data transformation unit is further configured to combine multiple data sources.

18. The control system of claim 16 wherein the data transformation unit is further configured to identify contextual information regarding the data from pre-existing knowledge bases and add the contextual information to the data.

19. A computer-implemented method for optimising a fuel generation process performed by a synthetic fuel generation plant, the computer-implemented method comprising:

obtaining an initial state associated with the synthetic fuel generation plant, the initial state comprising state information indicative of a state of one or more processes of the synthetic fuel generation plant at an initial time point;

determining contextual information regarding the initial state from a knowledge base and augment the data regarding the initial state with the contextual information;

obtaining a digital twin representative of the synthetic fuel generation plant, the digital twin comprising a trained machine learning model which in use:

receives a first state associated with the synthetic fuel generation plant at a first time point; and predicts a first future state, wherein the first future state comprises predicted state information indicative of a future state of one or more processes of the synthetic fuel generation plant at a second time point subsequent the first time point;

obtaining an objective function which in use maps from a given state to an objective value for said given state, wherein the objective value for the given state is indicative of an estimated quantity and/or quality of synthetic fuel generated by the one or more processes when the synthetic fuel generation plant is in the given state;

performing an optimisation process to determine an updated state from the initial state, the optimisation process comprising:

determining an initial future state for the initial state using the digital twin, wherein the initial future state comprises predicted state information indicative of the future state of one or more processes of the synthetic fuel generation plant at a future time point subsequent the initial time point; and optimising the objective function to obtain the updated state such that a first objective value determined by the objective function for an updated future state is greater than a second objective value determined by the objective function for the initial future state;

wherein the updated future state is determined from the updated state by the digital twin, and the updated future state comprises predicted state information indicative of the future state of one or more processes of the synthetic fuel generation plant at the future time point; and providing an evaluation of the updated future state based on the updated future state information and the contextual information.

20. A non-transitory computer readable storage medium comprising one or more program instructions which, when executed by one or more processors, cause the one or more processors to perform the steps of:

obtaining an initial state associated with a synthetic fuel generation plant, the initial state comprising state information indicative of a state of one or more processes of the synthetic fuel generation plant at an initial time point;

determining contextual information regarding the initial state from a knowledge base and augment the data regarding the initial state with the contextual information;

obtaining a digital twin representative of the synthetic fuel generation plant, the digital twin comprising a trained machine learning model which in use:

receives a first state associated with the synthetic fuel generation plant at a first time point; and predicts a first future state, wherein the first future state comprises predicted state information indicative of a future state of one or more processes of the synthetic fuel generation plant at a second time point subsequent the first time point;

obtaining an objective function which in use maps from a given state to an objective value for said given state, wherein the objective value for the given state is indicative of an estimated quantity and/or quality of synthetic fuel generated by the one or more processes when the synthetic fuel generation plant is in the given state;

performing an optimisation process to determine an updated state from the initial state, the optimisation process comprising:

determining an initial future state for the initial state using the digital twin, wherein the initial future state comprises predicted state information indicative of the future state of one or more processes of the synthetic fuel generation plant at a future time point subsequent the initial time point; and optimising the objective function to obtain the updated state such that a first objective value determined by the objective function for an updated future state is greater than a second objective value determined by the objective function for the initial future state;

wherein the updated future state is determined from the updated state by the digital twin, and the updated future state comprises predicted state information indicative of the future state of one or more processes of the synthetic fuel generation plant at the future time point; and providing an evaluation of the updated future state based on the updated future state information and the contextual information.

* * * * *